United States Patent [19]

Yokoyama

[11] Patent Number: 6,046,044
[45] Date of Patent: Apr. 4, 2000

[54] CISPLATIN RESISTANCE PROTEINS

[76] Inventor: Shiro Yokoyama, 1-17-7, Miwamidoriyama, Machida-City, Tokyo 195, Japan

[21] Appl. No.: 08/852,865

[22] Filed: May 8, 1997

Related U.S. Application Data

[62] Division of application No. 08/224,983, Apr. 8, 1994, Pat. No. 5,646,011.

[51] Int. Cl.[7] .............................. C12N 9/02; C07K 14/47
[52] U.S. Cl. ........................... 435/189; 530/350; 530/300
[58] Field of Search ............................. 435/189; 530/350, 530/300

[56] References Cited

PUBLICATIONS

McKeage et al., (1994), "Mechanism of action of an orally administered platinum complex [ammine bis butyrato cyclohexylamine dichloroplatinum (IV) (JM221)] in intrinsically cisplatin–resistant human ovarian carcinoma in vitro", Br. J. Cancer, vol. 69, pp. 1–7.

Oldenburg et al. (1994), "Characterization of Resistance Mechanisms to cis–Diamminedichloroplatinum (II) in Three Sublines of the CC531 Colon Adenocarcinoma Cell Line in Vitro", Cancer Research, vol. 54, pp. 487–493.

Doyle, L.A., (1993), "Mechanisms of Drug Resistance in human Lung Cancer Cells", Seminars in Oncology, vol. 20, No. 4, pp. 326–337.

Gately, D P and Howell, S.B., (1993), "Cellular accumulation of the anticancer agent cisplatin. A Review", Br. J. Cancer, vol. 67, pp. 1171–1176.

Hrubisko et al, (1993), "The role of metallothionein, glutathione S–transferases and DNA repair in resistance to platinum drugs in a series of L1210 cell lines made resistant to anticancer platinum agents", Biochemical Pharmacology, vol. 45, No. 1, pp. 253–256.

Morton et al. (1993), "Enrichment for Metallothionein Does Not Confer Resistance to Cisplatin in Transfected NIH/3T3 Cells", The Journal of Pharmacology and Experimental Therapeutics, vol. 267, No. 2, pp. 697–702.

Koropatrick, J and Pearson J., (1993), "Altered Cisplatin and Cadmium Resistance and Cell Survival in Chinese Hamster Ovary Cells Expressing Mouse Metallothionein", Molecular Pharmacology, vol. 44, pp. 44–50.

Eicnholtz–Wirth et al., (1993), "Radiation–induced transient cisplatin resistance in murine fibrosarcoma cells associated with elevated metallothionein content", Br. J. Cancer, vol. 67, pp. 1001–1006.

Wood et al, (1993), "Metallothionein Gene Expression in Bladder Cancer Exposed to Cisplatin", Modern Pathology, vol. 6, No. 1, pp. 33–35.

Hamaguchi et al., (1993), "Cross–Resistance to Diverse Drugs Is Associated with Primary Cisplatin Resistance in Ovarian Cancer Cell Lines", Cancer Research, vol. 53, pp. 5225–5232.

Godwin et al, (1992), "High resistance to cisplatin in human ovarian cancer cell lines is associated with marked increase of glutathione synthesis", Proceedings of the National Academy of Science, vol. 89, pp. 3070–3074.

Lu, X. et al (1992) "Differentiation of HT–29 Human Colonic Adenocarcinoma Cells Correlates with Increased Expression of Mitochondrial RNA: Effects of Trehalose on Cell Growth and Maturation" Cancer Research, 52:3718–3725.

Meijer et al., (1992), "Relationship of Cellular Glutathione to the Cytotoxicity and Resistance of Seven Platinum Compounds", Cancer Research, vol. 52, pp. 6885–6889.

Niimi et al., (1991), "Resistance to anticancer drugs in NIH3T3 cells transfected with c–myc and/or c–H–ras genes", Br. J. Cancer, vol. 63, pp. 237–241.

Majander et al. (1991), "Electron transfer properties of NADH: ubiquinone reductase in the ND1/3460 and the ND4/11778 mutations of the Leber hereditary optic neuroretinopathy (LHON)", FEBS, vol. 292, No. 1,2, pp. 289–292.

Howell et al, (1991), "Leber Hereditary Optic Neuropathy. Identification of the Same Mitochondrial ND1 mutation in Six Pedigrees", Am J. Hum. Genet., vol. 49, pp. 939–950.

Kasahara et al., (1991), "Metallothionein Content Correlates with the Sensitivity of Human Small Cell Lung Cancer Cell Lines to Cisplatin", Cancer Research, vol. 51, pp. 3237–3242.

Puchalski et al., (1990), "Expression of recombinant glutathione S–transferase π, Ya, or $Yb_1$ confers resistance to alkylating agents", Proceedings of the National Academy of Sciences, vol. 87, pp. 2443–2447.

Miyazaki et al, (1990), "Drug Resistance to Cis–Diamminedichloroplatinum (II) in Chinise Hamster Ovary Cell Lines Transfected with Glutathione S–transferase PI Gene", Biochemical and Biophysical Research Communications, vol. 166, No. 3, pp. 1358–1364.

(List continued on next page.)

Primary Examiner—Charles L. Patterson, Jr.
Assistant Examiner—Gabriele E. Bugaisky
Attorney, Agent, or Firm—Lahive & Cockfield, LLP; Giulio A. DeConti, Jr., Esq.; Catherine J. Kara

[57] ABSTRACT

Isolated nucleic acids which can confer on a cell at least a 5-fold increase in cisplatin resistance relative to a cisplatin sensitive cell are disclosed. The nucleic acids of the invention can farther confer on a cell resistance to heavy metals such as cadmium and copper. Isolated proteins encoded by the nucleic acids of the invention are also disclosed. The isolated nucleic acids and proteins of the invention are useful for conferring cisplatin resistance on a cell, for example non-malignant cells in a tumor bearing subject being treated with cisplatin. Alternatively, the cisplatin resistance of a cell can be inhibited by contacting the cell with an agent which inhibits the activity of the protein of the invention, for example to reverse the cisplatin resistance of a tumor cell. The invention also discloses methods for identifying substances which inhibit cisplatin resistance in a cell or which are chemosensitizers of cisplatin. The invention further discloses methods for identifying cisplatin resistant tumor cells using the nucleic acids and proteins of the invention.

8 Claims, 13 Drawing Sheets

OTHER PUBLICATIONS

Sabun et al, (1989), "Increased Expression of Glutathione S–Transferase Gene in cis–Diamminedichloroplatinum(II)–resistant Variants of a Chinese Hamster Ovary Cell Line", *Cancer Research,* vol. 49, pp. 7020–7025.

Kelley et al, (1988), "Overexpression of Metallothionein Confers Resistance to Anticancer Drugs", *Science,* vol. 241, pp. 1813–1815.

Jacobs et al, (1988), "Nucleotide Sequence and Gene Organization of Sea Urchin Mitochondrial DNA", *J. Mol. Biol.,* vol. 202, pp. 185–217.

Hromas et al, (1987), "Glutathione Depletion Reverses Cisplatin Resistance in Murine L1210 Leukemia Cells", *Cancer Letters,* vol. 34, pp. 9–13.

Roe et al, (1985), "The Complete Nucleotide Sequence of the Xenopus Laevis Mitochondrial Genome", *The Journal of Biological Chemistry,* vol. 260, No. 17, pp. 9759–9774.

Nomiyama et al., (1985), "Molecular structures of mitochondrial–DNA–like sequences in human nuclear DNA", *Nucleic Acids Research,* vol. 13, No. 5, pp. 1649–1658.

Montoya et al., (1983), "The Pattern of Transcription of the Human Mitochondrial rRNA Genes Reveals Two Overlapping Transcription Units", *Cell,* vol. 34, pp. 151–159.

Anderson et al., (1982), "Complete Sequence of Bovine Mitochondrial DNA Conserved Features of the Mammalian Mitochondrial Genome", *J Mol. Biol ,* vol. 156, pp. 683–717.

Dubin et al., (1982), "Sequence Analysis and Precise Mapping of the 3' Ends of HeLa Cell Mitochondrial Ribosomal RNAs", *J. Mol. Biol.,* vol. 157, pp. 1–19.

Bibb et al., (1981), "Sequence and Gene Organization of Mouse Mitochondrial DNA", *Cell,* vol. 26, pp. 167–180.

Anderson et al., (1981), "Sequence and organization of the human mitochondrial genome", *Nature,* vol. 290, pp. 457–464.

Montoya et al, (1981), "Distinctive features of the 5'–terminal sequence of the human mitochondrial mRNAs", *Nature,* vol. 290, 465–470.

Yagi et al. Identification of the dicyclohexylcarbodiimide–binding subunit of NAH–ubiquinone oxidoreductase (complex I). J. Biol. Chem. 263(31): 16150–16155, Nov. 5, 1988.

Petros et al. Mitochondrial DNA deletion of the ND1 gene found in a renal cell carcinoma. J. Urology 151 (5 SUPPL): 486A, May 1994.

| | | |
|---|---|---|
| cDNA 62 Mitochon. | CTTAGCCAAACCATTTACCCAAATAAAGTATAGGCGATAG<br>........................................ | 40 |
| 62<br>M | AAATTGAAACCTGGCGCAATAGATATAGTACCGCAAGGGA<br>........................................ | 80 |
| 62<br>M | AAGATGAAAAATTATAACCAAGCATAATATAGCAAGGACT<br>........................................ | 120 |
| 62<br>M | AACCCCTATACCTTCTGCATAATGAATTAACTAGAAATAA<br>........................................ | 160 |
| 62<br>M | CTTTGCAAGGAGAGCCAAAGCTAAGACCCCCGAAACCAGA<br>........................................ | 200 |
| 62<br>M | CGAGATACCTAAGAACAGCTAAAAGAGCACACCCGTATAT<br>........................................ | 240 |
| 62<br>M | GTA<u>C</u>CAAAATAGTGGGAAGATTTATAGGTAGAGGCGACAA<br>...G.................................... | 280 |
| 62<br>M | ACCTACCGAGCCTGGTGATAGCTGGTTGTCCAAGATAGAA<br>........................................ | 320 |
| 62<br>M | TCTTAGTTCAACTTTAAATTTGCCCACAGAACCCTCTAAA<br>........................................ | 360 |
| 62<br>M | TCCCCTTGTAAATTTAACTGTTAGTCCAAAGAGGAACAGC<br>........................................ | 400 |
| 62<br>M | TCTTTGGACACTAGGAAAAACCTTGTAGAGAGTAAAA<br>........................................ | 440 |
| 62<br>M | AATTTAACACCCATAGTAGGCCTAAAAGCAGCCACCAATT<br>........................................ | 480 |
| 62<br>M | AAGAAAGCGTTCAAGCTCAACACCCACTACCTAAAAAATC<br>........................................ | 520 |
| 62<br>M | CCAAACATATAACTGAACTCCTCACACCCAATTGGACCAA<br>........................................ | 560 |
| 62<br>M | TCTATCACCCTATAGAAGAACTAATGTTAGTATAAGTAAC<br>........................................ | 600 |

FIGURE 6A

| 62 | ATGAAAACATTCTCCTCCGCATAAGCCTGCGTCAGATTAA | 640 |
| M | ........................................ | |

| 62 | AACACTGAACTGACAATTAACAGCCCAATATCTACAATCA | 680 |
| M | ........................................ | |

| 62 | ACCAACAAGTCATTATTACCCTCACTGTCAACCCAACACA | 720 |
| M | ........................................ | |

| 62 | GGCATGCTCATAAGGAAAGGTTAAAAAAGTAAAAGGAAC | 760 |
| M | ........................................ | |

| 62 | TCGGCAAATCTTACCCCGCCTGTTTACCAAAAACATCACC | 800 |
| M | ........................................ | |

| 62 | TCTAGCATCACCAGTATTAGAGGCACCGCCTGCCCAGTGA | 840 |
| M | ........................................ | |

| 62 | CACATGTTTAACGGCCGCGGTACCCTAACCGTGCAAAGGT | 880 |
| M | ........................................ | |

| 62 | AGCATAATCACTTGTTCCTTAAATAGGGACCTGTATGAAT | 920 |
| M | ........................................ | |

| 62 | GGCTCCACGAG<u>G</u>TTCAGCTGTCTCTTACTTTTAACCAGTG | 960 |
| M | ...........<u>_</u>............................ | |

| 62 | AAATTGACCTGCCCGTGAAGAGGCGGGCAT<u>G</u>ACACAGCAA | 1000 |
| M | ..............................A......... | |

| 62 | GACGAGAAGACCCTATGGAGCTTTAATTTATTAATGCAAA | 1040 |
| M | ........................................ | |

| 62 | CAGTACCTAACAAACCCACAGGTCCTAAACTACCAAACCT | 1080 |
| M | ........................................ | |

| 62 | GCATTAAAAATTTCGGTTGGGGCGACCTCGGAGCAGAACC | 1120 |
| M | ........................................ | |

| 62 | CAACCTCCGAGCAGTACATGCTAAGACTTCACCAGTCAAA | 1160 |
| M | ........................................ | |

| 62 | GCGAACTACTATACTCAATTGATCCAATAACTTGACCAAC | 1200 |
| M | ........................................ | |

FIGURE 6B

| | | |
|---|---|---|
| 62 | GGAACAAGTTACCCTAGGGATAACAGCGCAATCCTATTCT | 1240 |
| M | .......................................  | |
| 62 | AGAGTCCATATCAACC-AATAGGGTTTACGACCTCGATGTT | 1280 |
| M | ...............CCC...................... | |
| 62 | GGATCC-AGGACATCCCGATGGTGCAGCCGCTATTAAAGGT | 1320 |
| M | ...TCCC................................. | |
| 62 | TCGTTTGTTCA<u>G</u>CGATTAAAGTCCTACGTGATCTGAGTTC | 1360 |
| M | ...........A........................... | |
| 62 | AGACCGGAGTAATCCAGGTCGGTTTCTATCTAC-TTCAAAT | 1400 |
| M | ................................CC...... | |
| 62 | TCCTCCCTGTACGAAAGGACAAGAGAAATAAGGCCTACTT | 1440 |
| M | ........................................ | |
| 62 | CACAAAGCGCCTTCCCCCGTAAATGATATCATCTCAACTT | 1480 |
| M | ........................................ | |
| 62 | AGTATTATACCCACACCCACCCAAGAACAGGGTTTGTTAA | 1520 |
| M | ........................................ | |
| 62 | GATGGCAGAGCCCGGTAATCGCATAAAACTTAAAACTTTA | 1560 |
| M | ........................................ | |
| 62 | CAGTCAGAGGTTCAATTCCTCTTCTTAACAACATACCCAT | 1600 |
| M | ........................................ | |
| 62 | GGCCAACCTCCTACTCCTCATTGTACCCATTCTAATCGCA | 1640 |
| M | ........................................ | |
| 62 (ORF) | M  A  N  L  L  L  I  V  P  I  L  I  A | |
| ND1 | ........................................ | |
| 62 | ATGGCATTCCTAATGCTTACCGAACGAAAAATTCTAGGCT | 1680 |
| M | ........................................ | |
| 62 (ORF) | M  A  F  L  M  L  T  E  R  K  I  L  G | |
| ND1 | ........................................ | |
| 62 | ATATACAACTACGCAAAGGCCCCAACGT<u>T</u>GTAGGCCCCTA | 1720 |
| M | ............................G........... | |
| 62 (ORF) | Y  I  Q  L  R  K  G  P  N  V  V  G  P | |
| ND1 | ........................................ | |

FIGURE 6C

| | | |
|---|---|---|
| 62 | CGGGCTACTACAACCCTTCGCTGACGCCATAAAACTCTTC | 1760 |
| M | ........................................ | |
| 62(ORF) | Y  G  L  L  Q  P  F  A  D  A  I  K  L  F | |
| ND1 | ........................................ | |
| 62 | ACCAAAGAGCCCCTAAAACCCGCCACATCTACCATCACCC | 1800 |
| M | ........................................ | |
| 62(ORF) |    T  K  E  P  L  K  P  A  T  S  T  I  T | |
| ND1 | ........................................ | |
| 62 | TCTACATCACCGCCCCGACCTTAGCTCTCACCATCGCTCT | 1840 |
| M | ........................................ | |
| 62(ORF) |    L  Y  I  T  A  P  T  L  A  L  T  I  A | |
| ND1 | ........................................ | |
| 62 | TCTACTATGAACCCCCCCTCCCCATACCCAATCCCCTGGT | 1880 |
| M | ........................................ | |
| 62(ORF) |    L  L  L  * | |
| ND1 | .........W | |
| 62 | CAACCTCAACCTAGGCCTCCTATTTATTCTAGCCACCTCT | 1920 |
| M | ........................................ | |
| 62 | AGCCTAGCCGTTTACTCAATCCTCTGATCAGGGTGAGCAT | 1960 |
| M | ........................................ | |
| 62 | CAAACTCAAACTACGCCCTGATCGGCGCACTGCGAGCAGT | 2000 |
| M | ........................................ | |
| 62 | AGCCCAAACAATCTCATATGAAGTCACCCTAGCCATCATT | 2040 |
| M | ........................................ | |
| 62 | CTACTATCAACATTACTAATAAGTGGCTCCTTTAACCTCT | 2080 |
| M | ........................................ | |
| 62 | CCACCCTTATCACAACACAAGAACACCTCTGATTACTCCT | 2120 |
| M | ........................................ | |
| 62 | GCCATCATGACCCTTGGCCATAATATGATTTATCTCCACA | 2160 |
| M | ........................................ | |
| 62 | CTAGCAGAGACCAACCGAACCCCCTTCGACCTTGCCGAAG | 2200 |
| M | ........................................ | |

FIGURE 6D

```
62   GGGAGTCCGAACTAGTCTCAGGCTTCAACATCGAATACGC    2240
M    ........................................

62   CGCAGGCCCCTTCGCCTTATTCTTCATAGCCGAATACACA    2280
M    ....................C...................

62   AACATTATTATAATAAACACCCTCACCACTACAATCTTCC    2320
M    ........................................

62   TAGGAACAACATAAGACGCACTCTCCCCTGAACTCTACAC    2360
M    ........................................

62   AACATATTTGTTACCAAGACCCTACTTCTAACCTCCCTG    2400
M    ...........C............................

62   TTCTTATGAATTCGAACAGCATACCCCCGATTCCGCTACG    2440
M    ........................................

62   ACCAACTCATACACCTCCTATGAAAAAACTTCCTACCACT    2480
M    ........................................

62   CACCCTAGCATTACTTATATGATATGTCTCCATACCCATT    2520
M    ........................................

62   ACAATCTCCAGCATTCCCCCTCAAACCTAAAAAAAAAAAA    2560
M    ........................................

62   AAAA                                      2564
M    ....
```

FIGURE 6E

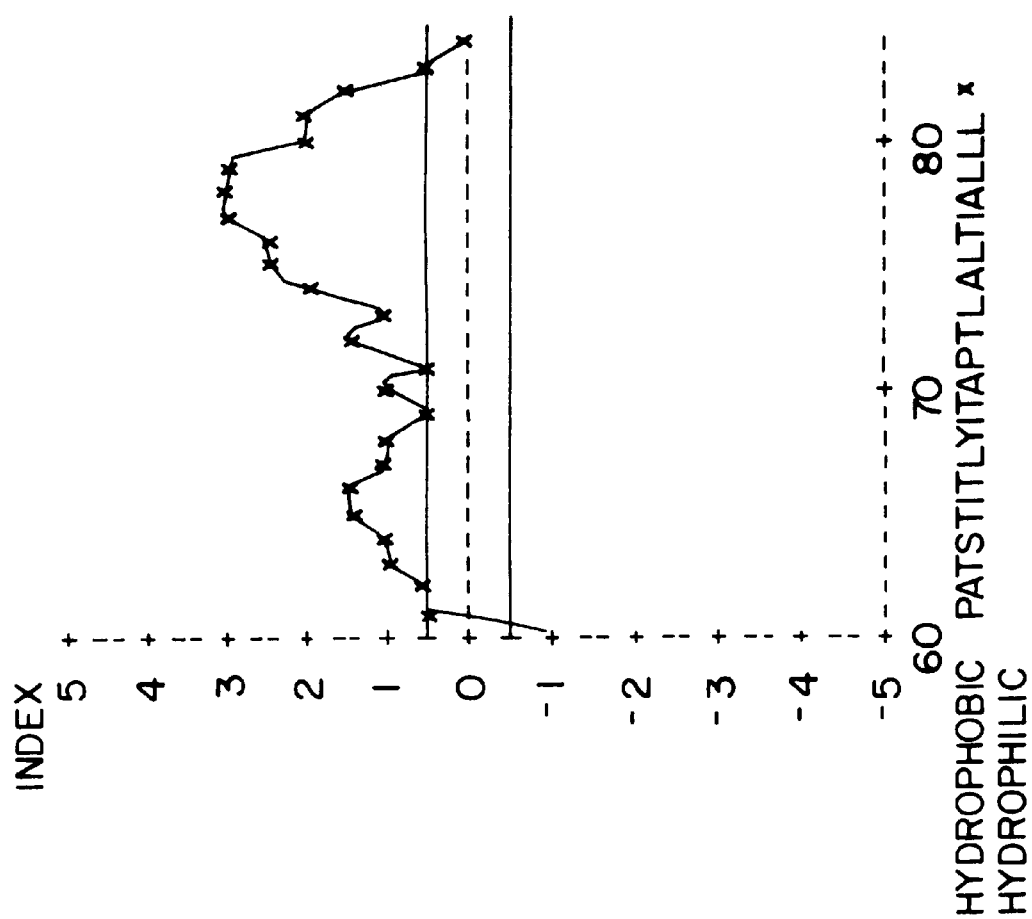

CISPLATIN RESISTANCE PROTEINS

This application is a divisional application of Ser. No. 08/224,983, filed on Apr. 8, 1994, U.S. Pat. No. 5,646,011. The contents of all of the aforementioned application(s) are hereby incorporated by reference.

BACKGROUND OF THE INVENTION

The chemotherapeutic drug cisplatin (cis-diamminedichloroplatinum or CDDP) was discovered to have cytotoxic properties in 1968 and is used extensively worldwide in the treatment of many tumors, in particular solid tumors such as ovarian cancer, testicular cancer and head and neck cancers. This platinum drug is thought to act by platination of DNA, thereby crosslinking DNA (both interstrand and intrastrand) and disrupting cellular processes. The clinical effectiveness of cisplatin is limited by the occurrence of cisplatin-resistant cancer cells. Certain tumors exhibit intrinsic or natural resistance to cisplatin and undergo no regression even upon initial chemotherapeutic treatment. Other tumors respond well to initial treatment but upon relapse exhibit reduced responsiveness to the drug. This type of resistance, which occurs after a course of therapy with cisplatin, is termed acquired resistance. The ability to prevent, overcome or reverse cisplatin resistance would be of great benefit to the treatment of malignant diseases.

Attempts have been made to identify the mechanism of cisplatin resistance but this mechanism remains to be elucidated. In various studies, cisplatin resistance has been associated with reduced intracellular accumulation of the drug, increased DNA repair function and/or increased drug detoxification by intracellular thiols (for reviews of possible mechanism of cisplatin resistance see e.g. Andrews, P. A. and Howell, S. B. (1990) *Cancer Cells* 2:35–43; Kelley, S. L. and Rozencweig, M. (1989) *Eur. J. Clin. Oncol.* 25:1135–1140; Perez, R. P. et al. (1990) *Pharmacol. Ther.* 48:19–27; and Timmer-Bosscha, H. et al. (1992) *Br. J Cancer* 66:227–238). A role for drug detoxification by intracellular thiols has been postulated due to an association of cisplatin resistance in certain cancer cell lines with increased levels of glutathione and metallothionein (see e.g. Godwin, A. K. et al. (1992) *Proc. Natl. Acad. Sci. USA* 89:3070–3074; and Kelley, S. L. et al. (1988) *Science* 241:1813–1815).

Attempts have also been made to implicate particular genes with acquisition of a cisplatin resistant phenotype. For example, glutathione-S-transferase (GST) and metallothionein genes have been transfected into cell lines to try to confer cisplatin resistance on the cells. GST has been reported to confer cisplatin resistance on cells but the level of increased resistance was only in the range of 1.5 to 3.0 fold (see e.g. Miyazaki, M. et al. (1990) *Biochem. Biophys. Res. Commun.* 166:1358–1364; and Puchalski, R. B. et al. (1990) *Proc. Natl. Acad. Sci. USA* 87:2443–2447). Another study has reported that transfection of cells with a metallothionein gene can confer cisplatin resistance on cells but again the level of increased resistance was less than 5-fold (see Kelley, S. L. et al. (1988) Science 241:1813–1815) and other studies found no increase in cisplatin resistance upon transfection of cells with the metallothionein gene (see Morton, K. A. et al. (1993) *J. Pharmacol. Exp. Ther.* 267:697–702; and Koropatnick, J. and Pearson, J. (1993) *Molec. Pharmacol.* 44:44–50). In another study, cells transfected with the c-myc gene were reported to have acquired resistance to cisplatin but once again the level of increased resistance was very low (i.e., less than 3-fold).

Multidrug resistance of tumor cells to anthracyclines (e.g. doxorubicin, epipodophyllotoxins and Vinca alkaloids) has been found to be associated with increased expression of one of two different genes, one encoding P-glycoprotein (see Roninson, I. B. et al. (1984) *Nature* 309:626–628; and Riordan, J. R. et al. (1985) *Nature* 316:817–819) and the other encoding MRP (see Cole, S. P. C. et al. (1992) *Science* 258:1650–1654). Transfection of cells with the mdr1 gene (encoding P-glycoprotein) or with the MRP gene can confer multidrug resistance on the cells (see Gros, P. et al. (1986) *Nature* 323:728–731; and Cole, S. P. C. (1994) *Cancer Res.* 54:357–361). However, neither P-glycoprotein or MRP are able to confer on a cell high level resistance to cisplatin and therefore do not account for cisplatin resistance observed in tumor cells.

None of studies described above convincingly account for the observed intrinsic or acquired cisplatin resistance of tumor cells. Thus, it can be concluded that a cisplatin resistance-determining gene, which can confer high levels of cisplatin resistance on a cell, remains to be identified.

SUMMARY OF THE INVENTION

This invention pertains to an isolated nucleic acid molecule which can confer high level cisplatin resistance on a cell in which the nucleic acid is expressed. In a preferred embodiment, expression of the nucleic acid of the invention in a cell confers on the cell at least a 5-fold increase in cisplatin resistance relative to a cisplatin sensitive cell. More preferably, resistance is increased at least 10- to 15-fold. Thus, the nucleic acid of the invention functions as a cisplatin resistance-determining gene. The invention is based, at least in part, on the isolation of a cDNA from a cisplatin resistant ovarian cancer cell line by differential cDNA library screening and the discovery of both its association with cisplatin resistance and its ability to confer high level cisplatin resistance on a cisplatin sensitive cell when introduced into the cell. The nucleic acid of the invention further can confer on a cell resistance to heavy metals such cadmium and copper. In one embodiment, the nucleic acid of the invention comprises a nucleotide sequence shown in SEQ ID NO: 1, or substantially similar thereto. The invention provides isolated nucleic acids which can confer cisplatin resistance on a cisplatin sensitive cell, nucleic acids which are antisense thereto, recombinant expression vectors comprising the nucleic acids of the invention (either sense or antisense), host cells comprising the recombinant expression vectors of the invention and transgenic and homologous recombinant non-human animals comprising the nucleic acids of the invention.

The invention further pertains to an isolated protein which can confer high level cisplatin resistance on a cell in which the protein is expressed. In a preferred embodiment, the protein of the invention can confer at least a 5-fold increase in cisplatin resistance on a cell when expressed in the cell. More preferably, resistance is increased at least 10- to 15-fold. The protein can further confer on a cell resistance to heavy metals, such as cadmium and copper, when expressed in the cell. In one embodiment, the protein comprises an amino acid sequence shown in SEQ ID NO: 2, or substantially similar thereto. The invention provides isolated proteins which can confer cisplatin resistance on a cisplatin sensitive cell, antibodies which bind to the proteins of the invention and pharmaceutical compositions comprising the antibodies of the invention. The antibodies of the invention can be labeled with a detectable substance or with a substance having toxic or therapeutic activity.

The invention further pertains to methods for inhibiting resistance of a cell to cisplatin. Accordingly, the methods of the invention can be used to inhibit resistance of tumor cells to cisplatin, thereby enabling cisplatin to be used therapeutically against the cells. The methods involve contacting a cisplatin resistant cell with an agent that inhibits the activity of a protein which confers on the cell resistance to cisplatin. Preferably, the protein confers on the cell at least a 5-fold increase in cisplatin resistance relative to a sensitive cell. In one embodiment, the agent which inhibits the activity of the protein is a nucleic acid which is antisense to the nucleic acid encoding the protein. In another embodiment, the agent is a molecule which binds to the protein, for example an antibody. The antibody further can be labeled with a substance having toxic or therapeutic activity. In yet another embodiment, the agent is a small molecule, e.g. a drug, which inhibits the activity of the protein. The method can further comprise contacting the cell with cisplatin to inhibit growth of the cell.

The invention still further pertains to methods for conferring on a cell resistance to heavy metals, including cisplatin, cadmium and copper resistance. The methods are useful for protecting cells from the growth inhibitory effects of heavy metals, e.g. non-malignant cisplatin sensitive cells in a subject being treated with cisplatin. The methods involve introducing into the cell a nucleic acid (in a form suitable for expression of the nucleic acid in the cell) which can confer on the cell resistance to cisplatin, preferably at least a 5-fold increase relative to a cisplatin sensitive cell. In one embodiment, a nucleic acid of the invention is used to confer cisplatin resistance. In another embodiment, a mitochondrial ND1 gene, which is homologous to the nucleic acid of SEQ ID NO: 1, is used to confer cisplatin resistance.

Other aspects of the invention include screening assays which can be used to identify substances which are cytotoxic to a cisplatin resistant cell or which are chemosensitizers of cisplatin. These methods are useful for identifying substances which can be used therapeutically against cisplatin resistant cells (e.g. cisplatin resistant tumor cells) to inhibit the growth of the cells. In these methods, a nucleic acid which confers on a cell cisplatin resistance is introduced in the cell to create a cisplatin resistant cell. The nucleic acid can be a nucleic acid of the invention (e.g., SEQ ID NO: 1) or can be a mitochondrial ND1 gene. Next, the cisplatin resistant cell is contacted with a substance to be tested. In methods directed to identifying a chemosensitizer of cisplatin, the cell is contacted with cisplatin in the presence or absence of the substance to be tested. The cytotoxicity of the test substance, or of cisplatin together with the test substance, for the cell is then determined. Cells used in these screening assays can be, for example, cells transfected in vitro with a nucleic acid of the invention. Alternatively, the cells can be within a transgenic animal carrying a nucleic acid of the invention and the substances can be administered to the transgenic animal.

The invention also provides methods for identifying cisplatin resistant tumor cells. In one embodiment, the method involves contacting nucleic acid from tumor cells (e.g., mRNA or cDNA) with a nucleotide probe which hybridizes to a nucleic acid of the invention and identifying cisplatin resistant tumor cells based upon increased hybridization of the probe to the nucleic acid from tumor cells relative to cisplatin sensitive cells. In another embodiment, the method involves contacting a sample of tumor cells with a molecule which binds to a protein of the invention (e.g., an antibody), wherein the molecule is labeled with a detectable substance (e.g. a fluorescent marker, radioactive isotope or enzyme) and detecting the substance bound to the tumor cells as an indication of cisplatin resistance of the tumor cells.

BRIEF DESCRIPTION OF THE DRAWINGS

FIG. 6 shows the nucleotide sequence of cDNA62 (top line; SEQ ID NO: 1) compared to the nucleotide sequence of human mitochondrial DNA encompassing the 16S rRNA-tRNA$^{Leu}$-ND1-tRNA$^{Ile}$ genes (bottom line; as disclosed in Anderson, S. et al. (1981) Nature 290:457–465). Only nucleotide differences in mitochondrial DNA compared to cDNA62 are shown. The amino acid sequence of the open reading frame of cDNA62 (SEQ ID NO: 2) is also shown below the nucleotide sequence.

DETAILED DESCRIPTION OF THE INVENTION

Figure 1:
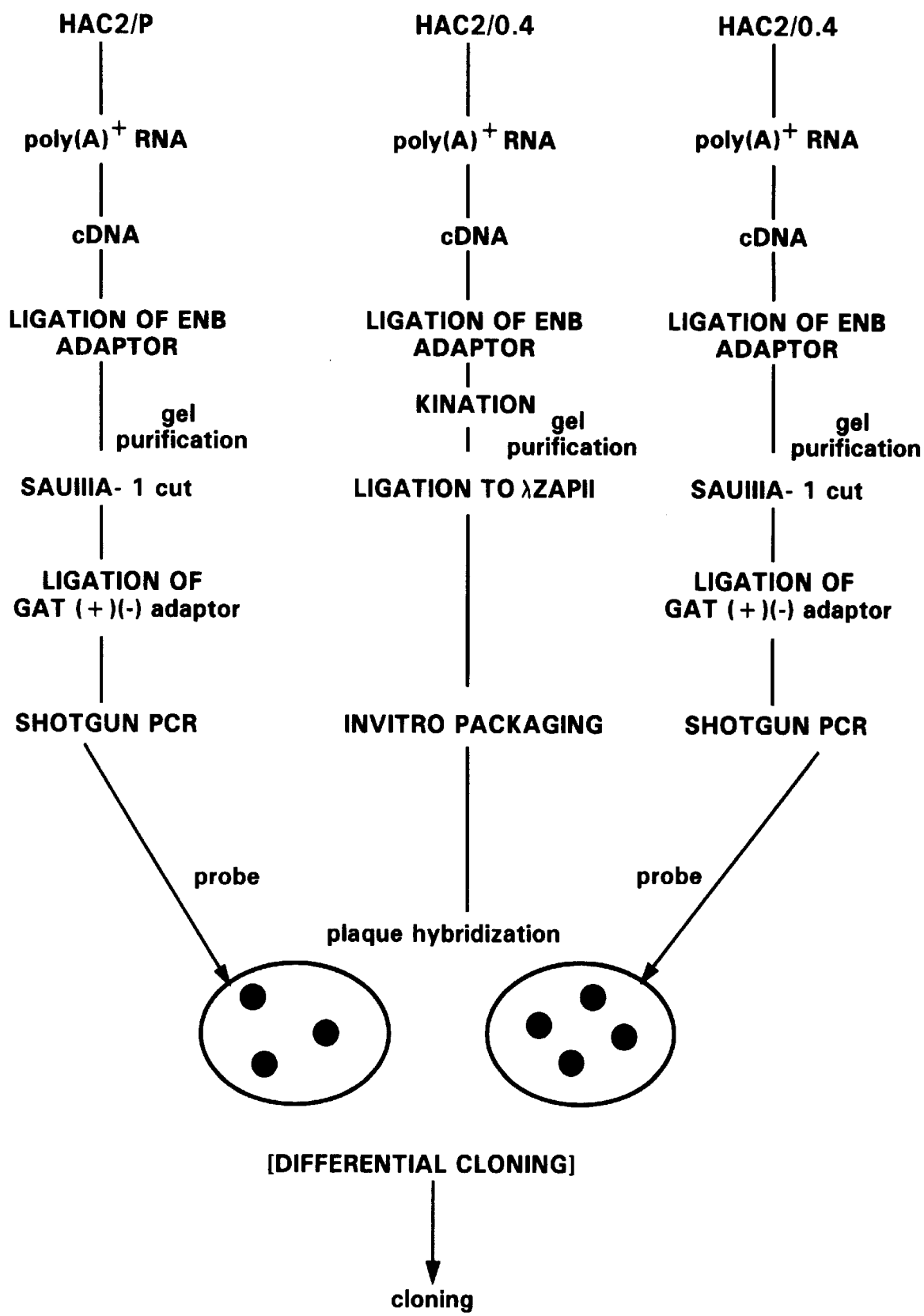
FIG. 1 is a schematic diagram of the differential cDNA library screening method used to isolate cDNA62.

The invention pertains to nucleic acids and proteins which can confer on a cell high level resistance to cisplatin when expressed in the cell. The invention is based, at least in part, on the isolation of a cisplatin resistance determining gene. As described in the Examples, a cDNA has been isolated from a cisplatin resistant ovarian cancer cell line by differential cDNA library screening. This cDNA (referred to herein as cDNA62) is expressed at a higher level in several cisplatin resistant cancer cell lines compared to their non-resistant parental cell lines and is expressed at a higher level in human tissues which are relatively more resistant to cisplatin compared to tissues which are relatively more sensitive to cisplatin. Thus, expression of cDNA62 is associated with cisplatin resistance. Moreover, expression of cDNA62, or the coding region thereof, in a cisplatin sensitive cell can confer on the cell high level cisplatin resistance (e.g., an 18-fold increase relative to a sensitive cell). cDNA62 can further confer on a cell in which it is expressed resistance to cadmium and copper (e.g., a 15-fold and 4-fold increase in resistance to cadmium and copper, respectively, relative to a sensitive cell). Thus, cDNA62 can be viewed as a heavy metal resistance determining gene, with cisplatin resistance being one kind of heavy metal resistance. Accordingly, for purposes of this invention, the term "heavy metal" is intended to include cisplatin, cadmium and copper.

Different aspects of the invention relate to isolated nucleic acids, antisense nucleic acids, recombinant expression vectors, host cells, transgenic and homologous recombinant non-human animals, isolated proteins, antibodies and methods involving inhibiting or conferring cisplatin resistance. The various aspects of the invention will be described in the following subsections.

I. Isolated Nucleic Acids

One aspect of the invention pertains to an isolated nucleic acid which confers on a cell in which the nucleic acid is expressed high level cisplatin resistance. "Resistance" of a cell to an agent (e.g., cisplatin) describes the ability of the cell to withstand without cytotoxicity increased concentrations of a drug as compared to a sensitive cell. Thus, cisplatin resistance of a cell is determined relative to an appropriate cisplatin sensitive cell. For example, the cisplatin resistance of a cell which has been continually exposed to the drug can be determined relative to the parental sensitive cell from which the drug resistant cell was derived. Alternatively, the cisplatin resistance of a cell into which has been introduced a nucleic acid which confers cisplatin resistance can be determined relative to the cisplatin sensitivity of the same cell which does not express the nucleic acid. The cisplatin resistance of naturally occurring tumor cells in vivo made drug resistant by continued exposure to a drug can be determined relative to the cisplatin sensitivity of the same tumor cells at the time of initial exposure to the drug. Resistance of a cell to an agent (e.g., cisplatin) is typically quantitated as the increase in $IC_{50}$ (concentration of the agent needed to inhibit cell growth by 50%) relative to a control sensitive cell.

A nucleic acid of the invention can confer on a cell in which the nucleic acid is expressed high level cisplatin resistance relative to a cisplatin sensitive cell. "Expression" of the nucleic acid refers to transcription of the nucleotide sequences comprising the nucleic acid into RNA. For purposes of the invention, high level cisplatin resistance is intended to mean at least a 5-fold increase in cisplatin resistance relative to a cisplatin sensitive cell. More preferably, the increase in resistance is at least 10-fold. Even more preferably, the increase in resistance is at least 15-fold. A nucleic acid of the invention can further confer on a cell in which it is expressed resistance to cadmium relative to a cadmium sensitive cell. Preferably, the increase in cadmium resistance is at least 3-fold, more preferably at least 5-fold, and even more preferably 8-fold. A nucleic acid of the invention can still further confer on a cell in which it is expressed resistance to copper relative to a copper sensitive cell. Preferably, the increase in copper resistance is at least 2-fold, more preferably at least 3-fold, and even more preferably 4-fold.

The invention provides isolated nucleic acids. The term "isolated" refers to a nucleic acid substantially free of cellular material or culture medium when produced by recombinant DNA techniques, or chemical precursors or other chemicals when chemically synthesized. An "isolated" nucleic acid is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded.

In a preferred embodiment, the nucleic acid of the invention which can confer high level resistance to cisplatin comprises a nucleotide sequence shown in SEQ ID NO: 1 (i.e., the nucleotide sequence of cDNA62, also shown in FIG. 6). The full-length cDNA62 (cDNA62F) in pBluescript SK- plasmid has been deposited at the National Institute of Bioscience and Human Technology in Tsukuba-shi, Ibaraki-ken 305, Japan, in compliance with the provisions of the Budapest Treaty, and has been assigned Deposit No. FERM BP-4629. In another embodiment, the nucleic acid comprises the coding region of the nucleotide sequence shown in SEQ ID NO: 1. The coding region of SEQ ID NO: 1 extends from nucleotide 1599 to nucleotide 1847. In another embodiment, the nucleic acid encodes a protein comprising an amino acid sequence shown in SEQ ID NO: 2.

As discussed in Example 3, the nucleotide sequence of cDNA62 (SEQ ID NO: 1) is approximately 99% identical to the nucleotide sequence of mitochondrial DNA extending from a portion of the 16S rRNA gene through the tRNA$^{Leu}$ gene and the ND1 gene up to the tRNA$^{Ile}$ gene. The two sequences are compared in FIG. 6. The nucleotide sequence of human mitochondrial DNA is disclosed in Anderson, S. et al. (1981) *Nature* 290:457–465. In part because of the differences in the nucleotide sequences of cDNA62 and mitochondrial DNA, it is thought that cDNA62 is encoded by a gene in nuclear DNA. Accordingly, in various embodiments, the nucleic acid of the invention comprises a nucleotide sequence which is identical to a nucleotide sequence naturally located in nuclear genomic DNA, thereby excluding nucleotide sequences present in mitochondrial DNA, e.g. the mitochondrial ND1 gene. The open-reading frame of SEQ ID NO: 1 encodes 83 amino acids (shown in SEQ ID NO: 2), with a stop codon at position 84. This amino acid sequence corresponds to the N-terminal 83 amino acids of the mitochondrial ND1 protein, which is a component of the NADH-ubiquinone oxidoreductase complex in mitochondria. However, amino acid position 84 is translated as tryptophan in mitochondrial ND1 mRNA transcripts and thus the mitochondrial ND1 protein extends beyond position 83. Accordingly, the 83 amino acid protein of SEQ ID NO: 2 is not produced by translation of the mitochondrial ND1 gene yet this protein is capable of conferring cisplatin resistance on a cell (see Example 4). Molecular structures in human nuclear DNA which have mitochondrial-DNA-like sequences have been described in the art (see e.g. Nomiyama H. et al. (1985) *Nucl. Acids Res.* 5:16491658).

It will be appreciated that the invention encompasses nucleic acids that can confer high level cisplatin resistance which have a nucleotide sequence which is substantially similar to the nucleotide sequence shown in SEQ ID NO: 1, or encoding a protein having an amino acid sequence which is substantially similar to the amino acid sequence shown in SEQ ID NO: 2. The term "substantially similar", in regards to a nucleotide or amino acid sequence, means those nucleotide and amino acid sequences which have slight or inconsequential sequence variations from the sequences disclosed in SEQ ID NO:1 and SEQ ID NO: 2, e.g. the homologous nucleic acid functions in substantially the same manner to produce substantially the same polypeptide having substantially the same activity as the actual sequence (e.g., the ability to confer cisplatin resistance on a cell). It is expected that substitutions or alterations can be made in the nucleotide or amino acid sequence without affecting function of the nucleic acid or protein encoded therein. For example, the degeneracy of the genetic code enables a number of amino acids to be designated by more than one triplet codon (for example, CAU and CAC both code for histidine). Thus, changes in the nucleotide sequence of SEQ ID NO: 1 (especially those within the third base of a codon) can be made which result in "silent" mutations in the DNA which do not affect the amino acid encoded. These silent mutations may occur naturally within. a population (DNA polymorphism) or can be introduced by standard recombinant DNA techniques. Additionally, it should be appreciated by those skilled in the art that DNA sequence polymorphisms that do lead to changes in the amino acid sequence shown in SEQ ID NO: 2 may exist within a population due to natural allelic variation, or can be created by standard techniques, without changing the functional activity of the protein. Accordingly, nucleic acids having a nucleotide sequence substantially similar to SEQ ID NO: 1 or encoding a protein having an amino acid sequence substantially similar to SEQ ID NO: 2 which retain the ability to confer at least a 5-fold increase in cisplatin resistance on a cell are intended to be encompassed by the invention.

In another embodiment, a nucleic acid of the invention hybridizes under high or low stringency conditions to a second nucleic acid. The second nucleic acid comprises the nucleotide sequence shown in SEQ ID NO: 1 or encodes a protein having an amino acid sequence shown SEQ ID NO:2. "High and low stringency conditions" are known to those skilled in the art or can be found in *Current Protocols in Molecular Biology*, John Wiley & Sons, N.Y. (1989), 6.3.1–6.3.6. For example, in filter hybridizations, stringency conditions are typically adjusted during washing of the filters after incubation of the filter with a nucleic acid probe under appropriate conditions for hybridization. During filter washing, non-specific or poorly hybridizing nucleic acids are removed from the filter as the stringency of the washing conditions are increased. Stringency conditions are typically adjusted by varying salt concentration (e.g., varying the concentration of a standard sodium citrate buffer, SSC) and/or varying temperature. A typical low stringency condition is about 2.0×SSC at about room temperature (e.g., about 22° C.). A typical high stringency condition is about 0.2×SSC at about 50° C. to 65° C.

A nucleic acid of the invention can be isolated from a cisplatin resistant cell line. One example of such a cell line is HAC2/0.4, which was produced as described in Example 1. Other suitable cell lines can be produced by stepwise selection of a non-resistant cell line in the presence of increasing concentrations of cisplatin over a period of time, typically several week to several months. The increase in fold resistance of the cell to cisplatin is assessed relative to the parental cell line from which the resistant cell line was derived (e.g., $IC_{50}$ of cisplatin for the resistant cell line versus the parental cell line). A nucleic acid of the invention can be isolated from a cisplatin resistant cell line (e.g., HAC2/0.4) by differential cDNA library screening, as described in detail in Example 1. Briefly, a cDNA library is constructed from total mRNA from HAC2/0.4 cells. The library is plated and two sets of replica filters are prepared by standard methods. One set of filters is then screened with cDNA prepared from HAC2/0.4 mRNA (e.g., by the "shotgun PCR" method described in Example 1) and the other set of filters is screened with a comparable amount of cDNA prepared from mRNA of the parental HAC2/P cell line. The cDNA used for screening the library is labeled, typically with a radioactive label. Following visualization of the hybridization results by standard procedures, cDNA clones displaying increased hybridization with HAC2/0.4 cDNA when compared to HAC2/P cDNA are selected from the library. These cDNAs are derived from mRNAs overexpressed in HAC2/0.4 relative to HAC2/P cells. For descriptions of differential cDNA library screening methods see King, C. R., et al. *J. Biol. Chem.* 254, 6781 (1979); Van der Bliek, A. M., et al., *Mol. Cell. Biol.* 6, 1671 (1986).

A nucleic acid of the invention can also be isolated by standard molecular biology techniques based upon the nucleotide sequence shown in SEQ ID NO: 1. For example, a labeled nucleic acid probe having a nucleotide sequence corresponding to all or part of SEQ ID NO: 1 can be used to screen a cDNA or genomic DNA library. For instance, a cDNA library made from a cisplatin resistant cell line as described above can be screened with a probe encompassing all or part of SEQ ID NO: 1. Alternatively, a nucleic acid of the invention can be isolated by selectively amplifying the nucleic acid using the polymerase chain reaction (PCR) method. For example, mRNA can be isolated from a cisplatin resistant cell line (e.g., by the guanidinium-thiocyanate extraction procedure of Chirgwin et al. (1979) *Biochemistry*, 18, 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla., are preferably employed). Synthetic oligonucleotide primers can be designed based upon the nucleotide sequence shown in SEQ ID NO: 1 for use in PCR. A nucleic acid of the invention can be amplified from cDNA (or, alternatively, genomic DNA) using these oligonucleotide primers and standard PCR amplification techniques. The nucleic acid so amplified can be cloned into an appropriate vector and characterized by DNA sequence analysis.

An RNA of the invention can be isolated by cloning a cDNA of the invention into an appropriate vector which allows for transcription of the cDNA to produce an RNA molecule. For example, a cDNA can be cloned downstream of a bacteriophage promoter, e.g. a T7 promoter, in a vector and the cDNA can be transcribed in vitro with T7 polymerase. A resultant RNA can be isolated by standard techniques.

A nucleic acid of the invention, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The isolated nucleic acids of the invention, or oligonucleotide fragments thereof, allow those skilled in the art to construct nucleotide probes for use in the detection of complementary nucleotide sequences in biological materials, such as tumor cell samples. Such molecular probes can be used diagnostically to identify cisplatin resistant tumor cells. A nucleotide probe can be labeled with a radioactive element which provides for an adequate signal as a means for detection and has sufficient half-life to be useful for detection, such as $^{32}P$, $^{3}H$, $^{14}C$ or the like. Other materials which can be used to label the probe include antigens that are recognized by a specific labeled antibody, fluorescent compounds, enzymes, antibodies specific for a labeled antigen, and chemiluminescent compounds. An appropriate label can be selected with regard to the rate of hybridization and binding of the probe to the nucleotide to be detected and the amount of nucleotide available for hybridization. Nucleic acids probes can be used, for example, in conventional dot blot, Northern hybridization or in situ hybridization procedures to probe mRNA molecules of total cellular or poly(A)+RNAs from a biological sample, e.g. cells of a tumor biopsy for diagnostic purposes. Additionally oligonucleotide primers designed based upon the nucleotide sequence of the nucleic acid of the invention can be used to amplify cDNA or genomic by PCR, e.g. to detect and quantitate expression of the nucleic acid in a cell sample (e.g. a tumor cell sample).

II. Antisense Nucleic Acids

The invention also relates to nucleic acids which are antisense to nucleic acids which can confer high level cisplatin resistance on a cell. An "antisense" nucleic acid comprises a nucleotide sequence which is complementary to a "sense" nucleic acid, e.g. complementary to an mRNA sequence encoding a protein, constructed according to the rules of Watson and Crick base pairing. Accordingly, an antisense nucleic acid can hydrogen bond to a sense nucleic acid. The antisense sequence complementary to a sequence of an mRNA can be complementary to a sequence found in the coding region of the mRNA or can be complementary to a 5' or 3' untranslated region of the mRNA. The coding region of the nucleotide sequence shown in SEQ NO 1: encompasses nucleotides 1599 to 1847. Preferably, an antisense nucleic acid is complementary to a region preceding or spanning the initiation codon or in the 3' untranslated region of an mRNA. An antisense nucleic acid can be designed based upon the nucleotide sequence shown in SEQ ID NO: 1. A nucleic acid is designed which has a sequence complementary to a sequence of the coding or untranslated region of the shown nucleic acid.

An antisense nucleic acid of the invention can be constructed using chemical synthesis and enzymatic ligation reactions using procedures known in the art. The antisense nucleic acid (e.g. an antisense oligonucleotide) can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acid can be produced biologically using an expression vector into which a nucleic acid has been subcloned in an antisense orientation (i.e. RNA transcribed from the inserted nucleic acid will be of an antisense orientation to a target nucleic acid of interest). The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986.

The antisense nucleic acids of the invention are useful for inhibiting expression of a nucleic acid (e.g. mRNAs) encoding a protein which confers on a cell cisplatin resistance, thereby decreasing expression of the protein. Decreasing expression of such a protein can be used as a means to inhibit or reverse the cisplatin resistance of a cell into which the antisense nucleic acid has been introduced. Antisense nucleic acids can be introduced into a cisplatin resistant cell in culture to inhibit expression of a protein of the invention. One or more antisense nucleic acids, such as oligonucleotides, can be added to cells in culture media, typically at about 200 μg/ml. A cultured cisplatin resistant cell in which expression of a protein of the invention has been inhibited is useful for testing the efficacy of potential therapeutic agents against the cell following inhibition of cisplatin resistance.

The antisense nucleic acids of the invention, or oligonucleotides thereof, can also be used in gene therapy to reverse or prevent cisplatin resistance in a subject. For example, antisense sequences can be used to render cisplatin resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotides thereof, can be directly introduced into tissues in vivo using delivery vehicles such as liposomes, retroviral vectors or adenoviral vectors. A delivery vehicle can be chosen which can be targeted to cells of interest in the subject (e.g. cisplatin resistant tumor cells).

In one embodiment, an antisense nucleic acid of the invention binds to the nucleic acid of SEQ ID NO: 1 but does not bind to a mitochondrial DNA. An antisense nucleic acid, e.g. an oligonucleotide, can be designed which spans a region of nucleotide sequence disparity between cDNA62 and mitochondrial DNA (the two sequences are compared in FIG. 6). Thus, this antisense nucleic acid can discriminate between a nucleic acid corresponding in sequence to cDNA62 and mitochondrial nucleic acid. Such an antisense nucleic acid may be useful for inhibiting cisplatin resistance in a cell without disrupting the function of the ND1 protein in mitochondria.

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a nucleic acid of the invention which confers cisplatin resistance can be designed based upon the nucleotide sequence of a nucleic acid of the invention. For example, a derivative of a Tetrahymena L-19 IVS RNA can be constructed in which the base sequence of the active site is complementary to the base sequence to be cleaved in a cisplatin resistance determining mRNA. See for example Cech et al. U.S. Pat. No. 4,987,071; and Cech et al. U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. (1993) *Science* 261, 1411–1418.

III. Recombinant Expression Vectors

The nucleic acids of the invention can be incorporated in a known manner into a recombinant expression vector which ensures good expression of the nucleic acid in a host cell. The recombinant expression vectors of the invention comprise a nucleic acid of the invention in a form "suitable for expression of the nucleic acid in a host cell", which means that the recombinant expression vectors includes one or more regulatory sequences, selected on the basis of the host cells to be used for expression, which is operatively linked to the nucleic acid. Operatively linked is intended to mean that the nucleic acid is linked to a regulatory sequence in a manner which allows for transcription of the nucleic acid into RNA. A recombinant expression vector thus can be used to express RNA (e.g, an antisense RNA) in a host cell or, more typically, is used to express a protein encoded by the RNA in a host cell. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids of the invention or to produce antisense nucleic acids.

The recombinant expression vectors of the invention can be designed for expression of encoded proteins in prokaryotic or eukaryotic cells. For example, proteins such be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, Calif. (1990).

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al, (1988) *Gene* 69:301–315) and the pET series of vectors (Studier et al., *Gene Expression Technology: Methods in Enzymology* 185, Academic Press, San Diego, Calif. (1990) 60–89). In pTrc, target gene expression relies on host RNA polymerase transcription from a hybrid trp-lac fusion promoter. In pET vectors, expression of inserted target genes relies on transcription from the T7 gn10-lac 0 fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention can be carried out by standard DNA synthesis techniques.

Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Expression of a nucleic acid of the invention in mammalian cells is accomplished using a mammalian expression vector. Examples of mammalian expression vectors include pCDM8 (Seed, B., (1987) *Nature* 329:840) and pMT2PC (Kaufman et al. (1987), *EMBO J*. 6:187–195). When used in mammalian cells, the expression vector's control functions are often provided by viral material. For example, commonly used promoters are derived from polyoma, Adenovirus 2, cytomegalovirus and most frequently, Simian Virus 40. In one embodiment, the PMAMneo expression vector (commercially available from Clontech) is used. In the pMAMneo vector, nucleic acid introduced into the vector is under the control of the MMTV LTR and polyadenylation signals from SV40. Additionally, a gene conferring neomycin resistance is encoded by the vector. In another embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein. Tissue-specific regulatory elements are known in the art.

The recombinant expression vector of the invention can be a plasmid. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The invention further provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleic acid of the invention, e.g. a nucleic acid comprising the nucleotide sequence of SEQ ID NO: 1. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA, as described above.

IV. Host Cells

The recombinant expression vectors of the invention can be introduced onto a cell, thereby creating a "host cell" of the invention. The term "host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate co-precipitation, DEAE-dextran-mediated transfection, lipofectin, electroporation or microinjection. Suitable methods for transforming and transfecting host cells can be found in Sambrook et al. (*Molecular Cloning: A Laboratory Manual*, 2nd Edition, Cold Spring Harbor Laboratory press (1989)), and other laboratory textbooks.

The number of host cells transformed with a recombinant expression vector of the invention by techniques such as those described above will depend upon the type of recombinant expression vector used and the type of transformation technique used. Plasmid vectors introduced into mammalian cells are typically integrated into host cell DNA at only a low frequency. In order to identify these integrants, a gene that contains a selectable marker (i.e., resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, more preferably, are introduced on a the same plasmid. Host cells transformed with a one or more recombinant expression vectors containing a nucleic acid of the invention and a gene for a selectable marker can be identified by selecting for cells using the selectable marker. For example, if the selectable marker encodes a gene conferring neomycin resistance (such as contained within the plasmid pMAMneo used in the Examples), transformant host cells can be selected with G418. Cells that have incorporated the selectable marker gene will survive, while the other cells die.

As demonstrated in the Examples, the nucleic acids of the invention can confer resistance to heavy metals (e.g., cisplatin, cadmium and copper) on a sensitive cell when transfected into the cell. Thus, it is possible for heavy metals to be used as selecting agents when preparing a host cell of the invention, rather than using an independent selectable marker (such as neomycin resistance). Therefore, the nucleic acids of the invention can be used as selectable markers for cells into which the nucleic acid has been introduced. See for example Pastan et al. U.S. Pat. No. 5,166, 059 and Croop et al. U.S. Pat. No. 5,198,344, which describe the use of the mdr 1 gene as a selectable marker. Cells are selected by exposure to one or more heavy metals. For example, a nucleic acid of the invention (e.g., in a recombinant expression vector) is introduced into a cell together with a second nucleic acid comprising a gene of interest, either in separate vectors or more preferably in the same vector. Transformant host cells are then selected based upon their acquired heavy metal resistance. Heavy metal resistant cells which are selected will contain the nucleic acid of the invention usually cointegrated with the gene of interest. Furthermore, by increasing stepwise the concentration of heavy metals used in selecting the cells, it is possible to obtain transformant host cells with a higher number of copies of the introduced nucleic acid, (including both the nucleic acid of the invention and a gene of interest). Therefore, the nucleic acids of the invention are also useful as amplifiable markers.

A host cell of the invention can be used to prepare an isolated protein encoded by a nucleic acid of the invention, ie. a protein which confers on a cell resistance to cisplatin. Accordingly, the invention provides a method for preparing an isolated protein which confers on a cell resistance to cisplatin. The method involves culturing a host cell of the invention in a suitable medium until a protein which confers on a cell resistance to cisplatin is formed and then isolating the protein. Suitable medium for culturing host cells are known in the art. For example, RPMI-1640 or DMEM, supplemented with additives as needed, e.g., serum, amino acids, buffers, antibiotics, etc. Proteins can be isolated from a host cell expressing the protein according to standard procedures of the art, including ammonium sulfate precipitation and fractionation column chromatography (e.g. ion exchange, gel filtration, electrophoresis, affinity chromatography, etc.). See generally, "Enzyme Purification and Related Techniques", *Methods in Enzymology*, 22, 233–577 (1971).

V. Isolated Proteins

The invention provides isolated proteins which can confer on a cell in which the protein is expressed high level resistance to cisplatin. For purposes of the invention, high level cisplatin resistance is intended to mean at least a 5-fold increase in cisplatin resistance relative to a cisplatin sensitive cell. More preferably, the increase in resistance is at least 10-fold. Even more preferably, the increase in resistance is at least 15-fold. A protein of the invention can further confer on a cell in which it is expressed resistance to cadmium relative to a cadmium sensitive cell. Preferably, the increase in cadmium resistance is at least 3-fold, more preferably at least 5-fold, and even more preferably 8-fold. A protein of the invention can still further confer on a cell in which it is expressed resistance to copper relative to a copper sensitive cell. Preferably, the increase in copper resistance is at least 2-fold, more preferably at least 3-fold, and even more preferably 4-fold.

An "isolated" protein refers to a protein substantially free of cellular material or culture medium when produced by recombinant DNA techniques, or chemical precursors or other chemicals when chemically synthesized.

In a preferred embodiment, the protein of the invention comprises an amino acid sequence shown in SEQ ID NO: 2. Other proteins which can confer high level cisplatin resistance on a cell and which are encoded by a nucleotide sequence present in nuclear DNA are also encompassed by the invention. In another embodiment, the protein of the invention comprises an amino acid sequence substantially similar to the amino acid sequence shown in SEQ ID NO: 2. As described in section I above regarding the nucleic acids of the invention, "substantially similar" amino acid sequences are intended to include amino acid sequences which have slight or inconsequential sequence variations from the sequence disclosed in SEQ ID NO: 2, i.e. the homologous protein functions in substantially the same manner as the protein comprising SEQ ID NO: 2 (e.g., can confer at least a 5-fold increase in cisplatin resistance on a cell in which the protein is expressed). In yet another embodiment, the protein of the invention is encoded by a nucleic acid which hybridizes under high or low stringency conditions to a second nucleic acid having a nucleotide sequence shown in SEQ ID NO: 1. In another embodiment, the protein of the invention is encoded by a nucleic acid which hybridizes under high or low stringency conditions to a second nucleic acid encoding a protein having the amino acid sequence shown in SEQ ID NO: 2.

In one embodiment, the protein of the invention is immunogenic. Immunogenic portions of the proteins of the invention are also within the scope of the invention. An immunogenic portion typically encompasses a region of the protein which is exposed on the surface of the protein, e.g. hydrophilic regions. The hydrophobicity of the protein of SEQ ID NO: 2 was analyzed and is plotted graphically in FIG. 7. The analysis reveals three hydrophilic stretches: amino acids 19–23, amino acids 27–33 and amino acids 52–60. Accordingly, polypeptides encompassing these hydrophilic regions are likely to be immunogenic and are encompassed by the invention.

A protein of the invention can be isolated by expression in a suitable host cell using techniques known in the art. Suitable host cells include prokaryotic or eukaryotic organisms or cell lines, for example, yeast, *E. coli* and insect cells. The recombinant expression vectors of the invention, described above, can be used to express a protein of the invention in a host cell in order to isolate the protein as described above.

Alternatively, the protein or portion thereof, can be prepared by chemical synthesis using techniques well known in the chemistry of proteins such as solid phase synthesis (Merrifield (1964) *J. Am. Chem. Assoc.* 85:2149–2154) or synthesis in homogeneous solution (Houbenweyl (1987) *Methods of Organic Chemistry*, ed. E. Wansch, Vol. 15 I and II, Thieme, Stuttgart).

VI. Antibodies

The proteins of the invention, or portions thereof, can be used to prepare antibodies which bind to the proteins. The term antibody as used herein is intended to include whole antibodies and fragments thereof which are also specifically reactive with a protein of the invention or peptide thereof. Antibodies can be fragmented using conventional techniques. For example, F(ab')$_2$ fragments can be generated by treating antibody with pepsin. The resulting F(ab')$_2$ fragment can be treated to reduce disulfide bridges to produce Fab' fragments.

Conventional methods can be used to prepare the antibodies, either polyclonal antisera or monoclonal antibodies. For example, a mammal, (e.g., a mouse, hamster, or rabbit) can be immunized with an immunogenic form of the protein or peptide which elicits an antibody response in the mammal. Techniques for conferring immunogenicity on a protein or peptide include conjugation to carriers or other techniques well known in the art. For example, the protein or peptide can be administered in the presence of an adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbor et al. (1983) *Immunol. Today* 4:72), and the EBV-hybridoma technique to produce human monoclonal antibodies (Cole et al. *Monoclonal Antibodies in Cancer Therapy* (1985) Allen R. Bliss, Inc., pages 77–96). Hybridoma cells can be screened immunochemically for production of antibodies specifically reactive with the protein or peptide and monoclonal antibodies isolated.

Another method of generating specific antibodies, or antibody fragments, reactive against protein of the invention, or peptide thereof, is to screen expression libraries encoding immunoglobulin genes, or portions thereof, expressed in bacteria with a protein or peptide of the invention. For example, complete Fab fragments, VH regions and FV regions can be expressed in bacteria using phage expression libraries. See for example Ward et al. (1989) *Nature* 345:544–546; Huse et al. (1989) *Science* 246:1275–1281; and McCafferty et al. (1990) *Nature* 348:552–554. Alternatively, the SCID-hu mouse can be used to produce antibodies, or fragments thereof.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing an immunoglobulin variable region which binds to a protein of the invention. See, for example, Morrison et al. (1985) *Proc. Natl. Acad. Sci. U.S.A.* 81: 6851; Takeda et al. (1985) *Nature* 314: 452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes a monoclonal or chimeric antibody of the invention can be further humanized by producing human variable region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al. (1983) *Proc. Natl. Acad. Sci. U.S.A.*, 80:7308–7312; Kozbor et al. (1983) *Immunology Today*, 4:7279; Olsson et al. (1982) *Meth. Enzymol.*, 92:3–16), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

The polyclonal or monoclonal antibodies of the invention can be coupled to a detectable substance. The term "coupled" is intended to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

An antibody of the invention can also be coupled to a substance having toxic or therapeutic activity. Examples of substances having toxic activity include radionuclides and toxins such as diptheria toxin and ricin or attenuated derivatives thereof. The term toxic substance is also intended to include cytotoxic cells such as macrophages, neutrophils, eosinophils, NK cells, LAK cells, and large granular lymphocytes. It will be appreciated that the antibody can be coupled to a cytotoxic cell through Fc receptors on cytotoxic cells. Examples of substances having therapeutic activity are chemotherapeutic agents such methotrexate.

The present invention allows the skilled artisan to prepare bispecific antibodies and tetrameric antibody complexes which bind to a protein of the invention. Bispecific antibodies can be prepared by forming hybrid hybridomas. The hybrid hybridomas can be prepared using the procedures known in the art such as those disclosed in Staerz & Bevan (*Proc. Natl. Acad. Sci. USA* (1986) 83:1453 and *Immunology Today* (1986) 7:241). In general, a hybrid hybridoma is formed by fusing a first cell line which produces a first monoclonal antibody which is capable of binding to a protein of the invention and a second cell line which produces a second monoclonal antibody which is capable of binding to a detectable substance, or a substance having toxic or therapeutic activity. The bispecific antibodies can also be constructed by chemical means using procedures such as those described by Staerz et al., (*Nature* (1985) 314:628) and Perez et al. (*Nature* (1985) 316:354).

A tetrameric antibody complex can be prepared by preparing a first monoclonal antibody which is capable of binding to protein of the invention and a second monoclonal antibody which is capable of binding to a detectable substance or a substance having toxic or therapeutic activity. The first and second antibody are from a first animal species. The first and second antibody are reacted with an about equimolar amount of antibodies of a second animal species or Fab fragments thereof, which are directed against the Fc-fragments of the antibodies of the first animal species. The tetrameric complex formed is then isolated. (See U.S. Pat. No. 4,868,109 to Lansdorp for a description of methods for preparing tetrameric antibody complexes).

As discussed previously, the protein of SEQ ID NO: 2 corresponds to the first 83 amino acids of the mitochondrial ND1 protein. In one embodiment, an antibody of the invention does not bind to the mitochondrial ND1 protein, i.e., the antibody can distinguish between the protein of SEQ ID NO: 2 and the mitochondrial ND1 protein. For example, an antibody (e.g. a monoclonal) which recognizes the unique conformation of the C-terminus of the protein of SEQ ID NO: 2 (which is not found in the ND1 protein) can be produced by standard techniques and selected by its ability to bind to the protein of SEQ ID NO: 2 but not the ND1 protein.

The antibodies of the invention (including monoclonal, bispecific and tetrameric antibody complexes) which bind a protein of the invention can be administered to a subject bearing a cisplatin resistant tumor, for example to detect the tumor or to treat the tumor (e.g., when the antibody is coupled to a toxic or therapeutic substance). Accordingly, the invention provides a pharmaceutical composition comprising an antibody of the invention and a pharmaceutically acceptable carrier. The term "pharmaceutically acceptable carrier" as used herein is intended to include diluents such as saline and aqueous buffer solutions. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. Pharmaceutical compositions suitable for injection use include sterile aqueous solutions (where water soluble) or dispersions and sterile powders for the extemporaneous preparation of sterile injectable solutions or dispersion. To administer an antibody by other than parenteral administration, it may be necessary to coat the antibody with, or co-administer the antibody with, a material to prevent its inactivation. Enzyme inhibitors include pancreatic trypsin inhibitor, diisopropylfluorophosphate and trasylol. Under ordinary conditions of storage and use, these preparations may contain a preservative to prevent the growth of microorganisms.

VII. Transgenic and Homologous Recombinant Animals

The nucleic acids of the invention can be used to generate either transgenic animals or homologous recombinant animals which, in turn, are useful in the screening of therapeutically useful reagents. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. Accordingly, in one embodiment, the invention provides a non-human transgenic animal which contains cells transfected to express a nucleic acid which confers on a cell resistance to cisplatin. Preferably, the non-human animal is a mouse, although the invention is not limited thereto. A transgenic animal can be created, for example, by introducing a nucleic acid encoding the protein (typically linked to appropriate regulatory elements, such as a tissue-specific enhancer) into the male pronuclei of a fertilized oocyte, e.g., by microinjection, and allowing the oocyte to develop in a pseudopregnant female foster animal. For example, a transgenic animal (e.g., a mouse) which expresses a nucleic acid which confers cisplatin resistance can be made using the isolated nucleic acid shown in SEQ ID NO: 1. Intronic sequences and polyadenylation signals can also be included in the transgene to increase the efficiency of expression of the transgene. These isolated nucleic acids can be linked to regulatory sequences which direct the expression of the encoded protein in one or more particular cell types. Methods for generating transgenic animals, particularly animals such as mice, have become conventional in the art and are described, for example, in U.S. Pat. Nos. 4,736,866 and 4,870,009 and Hogan, B. et al., (1986) A Laboratory Manual, Cold Spring Harbor, N.Y., Cold Spring Harbor Laboratory. A transgenic founder animal can be used to breed additional animals carrying the transgene.

The transgenic animals of the invention can be used to investigate the molecular basis of cisplatin resistance. The transgenic animals of the invention can also be used to test substances for the ability to prevent, slow or reverse the development of cisplatin resistance. A transgenic animal can be treated with the substance in parallel with an untreated control transgenic animal. Cells from the transgenic animals of the invention can be cultured using standard tissue culture techniques. In particular, cells carrying the recombinant molecule of the invention can be cultured and used to test substances for the ability to prevent, slow or reverse cisplatin resistance.

The isolated nucleic acids of the invention can further be used to create a non-human homologous animal. The term "homologous recombinant animal" as used herein is intended to describe an animal containing a gene which has been modified by homologous recombination. The homologous recombination event may completely disrupt the gene such that a functional gene product can no longer be produced (often referred to as a "knock-out" animal) or the homologous recombination event may modify the gene such that an altered, although still fumctional, gene product is produced. Accordingly, homologous recombination can be used to produce an animal which lacks or contains an altered cisplatin resistance determining gene. Preferably, the non-human animal is a mouse. For example, an isolated nucleic acid of the invention can be used to create a homologous recombinant mouse in which a recombination event has occurred in a cisplatin resistance determining gene. In one embodiment, the invention provides a non-human homologous recombinant animal containing cells having an altered gene which comprises the nucleotide sequence shown in SEQ ID NO: 1.

To create an animal with homologously recombined nucleic acid, a vector is prepared which contains the DNA sequences which are to replace the endogenous DNA sequences, flanked by DNA sequences homologous to flanking endogenous DNA sequences (see for example Thomas, K. R. and Capecehi, M. R. (1987) Cell 51:503). The vector is introduced into an embryonic stem cell line (e.g., by electroporation) and cells in which the introduced DNA has homologously recombined with the endogenous DNA are selected (see for example Li, E. et al. (1992) Cell 69:915). The selected cells are then injected into a blastocyst of an animal (e.g., a mouse) to form aggregation chimeras (see for example Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA.

VIII. Methods of the Invention

One aspect of the invention pertains to methods for inhibiting resistance of a cell to cisplatin. For example, the method can be used to inhibit the cisplatin resistance of tumor cells in a subject, thereby increasing the therapeutic efficacy of cisplatin against the tumor cells. Accordingly, a preferred cell type in which cisplatin resistance is inhibited is a tumor cell. In particular, solid tumors which exhibit cisplatin resistance, e.g. ovarian, testicular and head and neck tumors, can be the target cell type for application of the method.

The method involves contacting the cell with an agent which inhibits the activity of a protein expressed by the cell which confers on the cell cisplatin resistance, preferably at least 5-fold, 10-fold or 15-fold relative to a cisplatin sensitive cell. Preferably, the protein which confers on the cell cisplatin resistance comprises the amino acid sequence shown in SEQ ID NO: 2, or substantially similar thereto. Alternatively, the protein can comprise other embodiments of the protein of the invention (as described in section V above).

Since the protein of SEQ ID NO: 2 corresponds in amino acid sequence to the N-terminal 83 amino acids of the mitochondrial ND1 protein, it is reasonable to expect that the ND1 protein may be involved in cisplatin resistance. Thus, in another embodiment, the protein whose activity is inhibited is a mitochondrial ND1 protein. The term "mitochondrial ND1 protein" is intended to describe a protein which is encoded in mitochondrial DNA and is a component of the NADH-ubiquinone oxidoreductase complex. The amino acid sequence of a human ND1 protein is disclosed in Anderson, S. et al. (1981) *Nature* 290:457–465. The amino acid sequences of ND1 proteins from other species are disclosed in Bibb, M. J. et al. (1981) *Cell* 26:167–180 (mouse); Anderson, S. et al. (1982) *J. Mol. Biol.* 156:683–717 (bovine); Roe, B. A. et al. (1985) *J. Biol Chem.* 260:9759–9774 (X. laevis); and Jacobs, H. T. etal. (1988) *J. Mol. Biol.* 202:185–217 (sea urchin).

In one embodiment of the method, the agent that inhibits the activity of the protein is a nucleic acid which is antisense to the nucleic acid encoding the protein. The antisense nucleic acid is introduced into the cell to inhibit the activity of the protein (described in more detail in section II above). An antisense nucleic acid can inhibit expression of the protein in the cell by interfering with translation of the mRNA encoding the protein. Alternatively, a ribozyme which cleaves the mRNA encoding the protein can be used to inhibit production of the protein.

In another embodiment, the agent which inhibits the activity of the protein is a molecule which binds to the protein. A preferred molecule is an antibody or fragment thereof. A molecule (e.g. antibody) is bound to the protein to interfere with the function of the protein. The molecule which binds to the protein (e.g. antibody) can be coupled to a substance having toxic or therapeutic activity. The term "substance having toxic or therapeutic activity" as used herein is intended to include molecules whose action can destroy a cell, such as a radioactive isotope, a toxin (e.g. diptheria toxin or ricin), or a chemotherapeutic drug, as well as cells whose action can destroy another cell, such as cytotoxic cells. The molecule binding to the cisplatin resistant cells can be directly coupled to a substance having toxic or therapeutic activity (e.g. a ricin-linked monoclonal antibody), or may be indirectly linked to the substance. For example, a bispecific antibody which is capable of crosslinking a tumor cell and a cytotoxic cell can be used, thereby facilitating lysis of the tumor cell. A bispecific antibody can crosslink a tumor cell and the cytotoxic cell by binding to the Fc receptors of cytotoxic cells.

In yet another embodiment, the agent which inhibits cisplatin resistance of the cell is a small molecule, e.g. drug, which inhibits the activity of the protein. Small molecules which inhibit cisplatin resistance can be identified by screening assays such as those provided by the invention (see below) or can be created based upon principles of rational drug design, e.g., a molecule which can inhibit the activity of a protein of the invention can be designed based upon the structure of the protein.

The method for inhibiting cisplatin resistance of cells can be used with a subject in vivo. The term "subject" is intended to include humans and other mammals, e.g. monkeys, dogs, cats, rats, rabbits, mice and transgenic species thereof. For example, an antisense nucleic acid can be delivered to cells in vivo (e.g., tumor cells) by techniques which have been used in the art for in vivo gene therapy, e.g., using retroviral or adenoviral vectors, liposome encapsulation, or direct injection into a tumor site. Antibodies, or other molecules which bind to a cisplatin resistance protein can be delivered to cells in vivo by injection, e.g. intravenous injection or injection into a tumor site. A small molecule inhibitor of cisplatin resistance can be delivered to a subject by an appropriate route, e.g. i.v. or oral administration. Alternatively, the method can be used to inhibit cisplatin resistance of cells in vitro, for example by transfecting cells with an antisense expression vector or by culturing the cells with an antibody which binds the protein. These cells in vitro can be used, for example, to determine the contribution of the cisplatin resistance protein to cross-resistance to other agents (e.g., other heavy metals) and to identify conditions (e.g., other agents) which are cytotoxic to cells in which cisplatin resistance has been inhibited.

This method can further comprise contacting the cell with cisplatin to inhibit growth of the cell. Following inhibition of the activity of the cisplatin resistance protein, the cell will be once again sensitive to the effects of cisplatin. Accordingly, cisplatin can be used to inhibit the growth of the cell. In a subject, cisplatin can be administered to the subject. For cells in vitro, the cells can be cultured with cisplatin.

Another aspect of the invention is a method for conferring resistance to a heavy metal on a cell. In one embodiment, the heavy metal is cisplatin. In another embodiment, the heavy metal is cadmium. In yet another embodiment, the heavy metal is copper. This method is useful for protecting a heavy metal sensitive cell from cytotoxicity due to exposure to the heavy metal. For example, non-malignant cisplatin sensitive cells in a subject bearing a tumor can be protected from cytotoxicity when the subject is treated with cisplatin.

This method involves introducing into the cell a nucleic acid which confers on the cell high level cisplatin resistance relative to a cisplatin sensitive cell. Preferably, the increase in cisplatin resistance is at least 5-fold, more preferably 10-fold, even more preferably 15-fold. A preferred nucleic acid to be introduced into a cell comprises a nucleotide sequence shown in SEQ ID NO: 1, or a coding region thereof. However, other embodiments of the nucleic acid of the invention (as described in section I above) can be used. For example, the nucleic acid can comprise a nucleotide sequence substantially similar to SEQ ID NO: 1, can encode a protein with an amino acid sequence substantially similar to SEQ ID NO: 2, or can hybridize under low or high stringency conditions to the nucleic acid of SEQ ID NO: 1.

Given the high degree of homology between the nucleic acid of SEQ ID NO: 1 and a mitochondrial ND1 gene (as illustrated in FIG. 6), it is reasonable to expect that a mitochondrial ND1 gene can confer heavy metal resistance on a cell in which it is expressed. Accordingly, in one embodiment, the nucleic acid which confers cisplatin resistance on a cell is a mitochondrial ND1 gene. The term "mitochondrial ND1 gene" is intended to describe a gene which is present in mitochondrial DNA and which encodes a component of the NADH-ubiquinone oxidoreductase complex. Preferably the mitochondrial ND1 gene is a human ND1 gene, the nucleotide sequence of which is disclosed in Anderson, S. et al. (1981) *Nature* 290:457–465. The nucleotide sequences of ND1 genes from other species are disclosed in Bibb, M. J. et al. (1981) *Cell* 26:167–180 (mouse); Anderson, S. et al. (1982) *J. Mol. Biol.* 156:683–717 (bovine); Roe, B. A. et al. (1985) *J. Biol Chem.* 260:9759–9774 (*X. laevis*); and Jacobs, H. T. et al. (1988) *J. Mol. Biol.* 202:185–217 (sea urchin).

The nucleic acid which is introduced into the cell is "in a form suitable for expression of the nucleic acid in the cell", meaning that the nucleic acid is operatively linked to one or more regulatory sequences in a manner which allows for transcription of the nucleic acid into RNA in the cell. In a preferred embodiment, the nucleic acid is in a recombinant expression vector (as described in section III above). The nucleic acid can be introduced into the cell by a standard transfection technique such as those described in section IV above regarding production of host cells of the invention.

This method is useful in situations where resistance of a cell to cisplatin is desired. For example, a major dose-limiting factor for chemotherapeutic agents is their cytotoxicity for normal cells in a patient as well as tumor cells. In patients with cisplatin resistant tumors, increasing the dosage of cisplatin can be prohibited by the toxicity of cisplatin for normal cells. The side effects of cisplatin are known to include myelotoxicity and nephrotoxicity. Protecting nonresistant nontumor cells from the effects of cisplatin (and other heavy metals), by conferring on the cell cisplatin resistance, thus has major clinical importance. A nucleic acid of the invention can be introduced into a cell in vivo in a subject by techniques which have been used in the art for in vivo gene therapy, e.g., using retroviral or adenoviral vectors, liposome encapsulation, or direct injection into a target site (e.g., kidney cells to inhibit nephrotoxicity or myeloid cells or precursors thereof to inhibit myelotoxicity). Alternatively, cells can be modified ex vivo and returned to the subject. For example, hematopoictic stem cells, which are susceptible to the effects of chemotherapeutic agents, can be isolated from a subject, transfected with a nucleic acid of the invention in vitro (by standard transfection techniques) and reintroduced into the subject.

Cells on which heavy metal resistance has been conferred, according to methods provided by the invention, are further useful in screening assays for therapeutic agents that are effective against heavy metal (e.g. cisplatin) resistant cells. These agents include agents which are themselves cytotoxic for resistant cells or which are chemosensitizers of other therapeutic agents. As used herein, the term "chemosensitizer" refers to a substance which can increase the efficacy of a therapeutic agent against a resistant cell and/or decrease the resistance of a cell for a therapeutic agent. For example, verapamil is a chemosensitizer of P-glycoprotein-mediated multidrug resistance: in the presence of verapamil, a multidrug resistant cell is more susceptible to the cytotoxic effect of anthracyclines. These screening methods can be used, for example, to identify substances which may be of use therapeutically in subjects bearing a cisplatin resistant tumor (i.e., in situations where cisplatin is no longer an effective therapeutic agent due to natural or acquired resistance).

Accordingly, the invention provides a method for identifying a substance which is cytotoxic to a cisplatin resistant cell. The method involves introducing into a cell a nucleic acid which confers on the cell cisplatin resistance (preferably at least a 5-, 10- or 15-fold increase in cisplatin resistance relative to a cisplatin sensitive cell), thereby creating a cisplatin resistant cell, contacting the cisplatin resistant cell with a substance to be tested and determining cytotoxicity of the substance for the cell. Preferred nucleic acids are as discussed above with regard to methods for conferring heavy metal resistance on a cell. For example, in one embodiment, the nucleic acid comprises a nucleotide sequence shown in SEQ ID NO: 1, or a coding region thereof. In another embodiment, the nucleic acid comprises a mitochondrial ND1 gene. Additionally, other embodiments of the nucleic acids of the invention are also encompassed by the method. Cytotoxicity of a substance for the cell can be determined by standard techniques, for example an MTT assay as described in the Examples. A cell cultured in vitro can be used in the screening assay, for example the cell can be contacted with the substance by culturing the cell in the presence of the substance. Alternatively, the cell can be in a nonhuman transgenic animal and the substance to be tested can be administered to the nonhuman transgenic animal (i.e., the term "contacting the cell" is intended to include administering the substance to an animal). In the case of a transgenic animal, the nucleic acid of the invention is introduced into the animal, or an ancestor thereof, at an embryonic stage (e.g., into a fertilized oocyte and the oocyte is allowed to develop into an animal by standard techniques).

The invention further provides a method for identifying a substance which is a chemosensitizer of cisplatin. In the method, a cisplatin resistant cell is created by introducing into the cell a nucleic acid which confers on the cell cisplatin resistance. Preferred nucleic acids for creating a cisplatin resistant cell are as described above. The cisplatin sensitive cell is then contacted with cisplatin in the presence and absence of a substance to be tested and the resistance of the cell to cisplatin in the presence and absence of the substance to be tested is determined. A substance which is a chemosensitizer of cisplatin is identified based upon the ability of the substance to inhibit resistance of the cell to cisplatin. Cytotoxicity of cisplatin for the cell can be determined by standard techniques, e.g. an MTT assay. A cell cultured in vitro can be used in the screening assay, for example the cell can be contacted with cisplatin and the substance to be tested by culturing the cell with cisplatin and the substance. Alternatively, the cell can be in a nonhuman transgenic animal and cisplatin and the substance to be tested can be administered to the nonhuman transgenic animal (i.e., the term "contacting the cell" is intended to include administering cisplatin and the substance to an animal).

The screening methods of the invention (i.e., methods for identifying substances which are cytotoxic to a cisplatin resistant cell or for identifying a chemosensitizer of cisplatin) can alternatively be performed with a cancer cell line which has been rendered cisplatin resistant by continued exposure to cisplatin (e.g., created as described in Example 1). Accordingly, the screening methods of the invention can also be performed with the HAC2/0.4 cell line provided by the invention. The HAC2/0.4 cell line has been deposited at the National Institute of Bioscience and Human Technology in Tsukuba-shi, Ibaraki-ken 305, Japan, in compliance with the provisions of the Budapest Treaty, and has been assigned Deposit No. FERM BP-4628. To identify a substance which is cytotoxic to HAC2/0.4, the cell line can be incubated with a substance to be tested and the cytotoxicity of the substance for the cell line can be determined. To identify a chemosensitizer of cisplatin, the HAC2/0.4 cell line can be incubated with cisplatin in the presence and absence of the substance to be tested and the cytotoxicity of cisplatin for the cell line can be determined.

The invention further provides methods for identifying cisplatin resistant tumor cells. In one embodiment, the method involves contacting nucleic acid (e.g., mRNA or cDNA) from a sample of tumor cells with a nucleotide probe which hybridizes to a nucleic acid of the invention and identifying cisplatin resistant tumor cells based upon increased hybridization of the nucleotide probe to the nucleic acid from the tumor cells relative to cells which are not resistant to cisplatin. Preferably, the nucleotide probe hybridizes to the nucleotide sequence shown in SEQ ID NO: 1, or an oligonucleotide fragment thereof. Standard hybridization techniques can be used, e.g. Northern blotting, RNAase protection, dot blot hybridization, in situ hybridization etc. The method encompasses use of oligonucleotide primers which can amplify a nucleic acid of the invention by reverse transcriptase-PCR from a tumor cell sample. An increase in hybridization of the probe to a nucleic acid of the invention within tumor cells can be determined qualitatively (e.g., by the size of a band on a hybridization blot) or quantitatively, e.g. by using quantitative PCR.

In another embodiment, the method involves contacting a tumor cell with a molecule which binds to a protein of the invention, wherein the molecule is labeled with a detectable substance, and detecting the detectable substance bound to the tumor cell as an indication of a cisplatin resistant tumor cell. A preferred molecule for binding to the protein is an antibody. In one embodiment, the antibody does not bind to the mitochondrial ND1 protein, i.e. an antibody which distinguishes between the protein of SEQ ID NO: 2 and the ND1 protein (as described above in section VI) can be used. Antibodies labeled with a detectable substance, such as a fluorescent marker, an enzyme or a radioactive marker, can be used to identify cisplatin resistant tumor cells in a tumor sample or in vivo. A cisplatin resistant tumor cell can be identified by incubating an antibody of the invention, for example a monoclonal antibody, with a tumor cell to be tested for cisplatin resistance. Binding of the antibody to the tumor cell is indicative of the presence on the tumor cell of a protein of the invention. The level of antibody binding to the tumor cell can be compared to the level of antibody binding to a normal control cell, and increased binding of the antibody to the tumor cell as compared to the normal cell can be used as an indicator of cisplatin resistance. Binding of the antibody to a cell (e.g. a tumor cell to be tested or a normal control cell) is determined by detecting the detectable substance with which the antibody is labeled. The detectable substance may be directly coupled to the antibody, or alternatively, the detectable substance may be coupled to another molecule which can bind the antibody. For example, an antibody of the invention which has a rabbit Fc region (e.g. which was prepared by immunization of a rabbit) can be detected using a second antibody directed against the rabbit Fc region, wherein the second antibody is coupled to a detectable substance.

Cisplatin resistant tumor cells can be detected in a tumor sample in vitro or in vivo. For example, tumor tissue removed from a patient can be used as the tumor sample. A sample can be used immediately or the sample can be stored at temperatures below −20° C. A tissue section, for example, a freeze-dried or fresh frozen section of tumor tissue removed from a patient, thus can be used as the tumor sample. A tumor section on a microscope slide can be reacted with antibodies using standard immunohistochemistry techniques or with nucleic acid by standard in situ hybridization techniques. Additionally, if a single cell suspension of tumor cells is achievable, tumor cells can be reacted with antibody and analyzed by flow cytometry. Alternatively, a cisplatin resistant tumor cell can be detected in vivo in a subject bearing a tumor. Labeled antibodies can be introduced into the subject and antibodies bound to the tumor can be detected. For example, the antibody can be labeled with a radioactive marker whose presence and location in a subject can be detected by standard imaging techniques.

Reagents used for identifying a cisplatin resistant tumor, for example nucleotide probes specific for a nucleic acid of the invention and/or antibodies which bind a protein of the invention, can be incorporated into a diagnostic kit. The kit can contain standards to which a sample is compared. The various reagents can be included in the kit in suitable containers and the kit can include a holder for the containers. The diagnostic kit can also contain an instruction manual for use of the kit.

The invention is further illustrated by the following examples. However, the examples are merely intended to illustrate embodiments of the invention and are not to be construed to limit the scope of the invention. The contents of all references and published patents and patent applications cited throughout this application are hereby incorporated by reference.

EXAMPLE 1

Differential cDNA Library Screening and Isolation of cDNAs Preferentially Expressed in a Cisplatin Resistant Cell Line cDNAs preferentially expressed in a cisplatin resistant cell line were isolated using a differential cDNA library screening method. The protocol is summarized schematically in FIG. 1 and is described in detail below.

Establishment of a Cisplatin Resistant Cell Line

An ovarian cancer cell line (HAC/P) was obtained from a previously untreated patient. HAC2/P exhibited adherent growth and cytologically was an adenocarcinoma cell type. A cisplatin resistant subclone (HAC2/0.4) of the parental HAC2/P cell line was established as follows. After a single-cell suspension of the parental cell line was made by trypinization, the cells were diluted to a concentration of $1 \times 10^3$ cells/ml in RPMI-1640 media (Gibco, Grand Island, N.Y.). One ml aliquots of the diluted cell suspension were plated in 6-well plates (Linbo, Horsham, Pa.) with cisplatin at an initial concentration of 0.01 μg/ml. When colonies were observed after 7 days, a single colony was isolated and propagated in another dish with an increased concentration of cisplatin. This cloning procedure was repeated to establish the resistant subline. Isolated clones were exposed to higher concentrations of cisplatin for 4 weeks until finally a clone which grew at a concentration of 0.4 μg/ml of cisplatin was obtained. HAC2/0.4 was cultured in an RPMI-1640-based culture medium in a humidified atmosphere of 5% $CO_2$ at 37° C. The cisplatin resistant phenotype of HAC2/0.4 was stable for more than 5 months even when cultured in the absence of cisplatin. Differential cloning experiments with HAC2/0.4 were performed 1 week after culturing in the absence of cisplatin.

The HAC2/0.4 cell line has been deposited at the National Institute of Bioscience and Human Technology in Tsukuba-shi, Ibaraki-ken 305, Japan, in compliance with the provisions of the Budapest Treaty, and has been assigned Deposit No. FERM BP-4628.

Preparation of cDNA and Construction of a HAC2/0.4 cDNA Library

Figure 2:
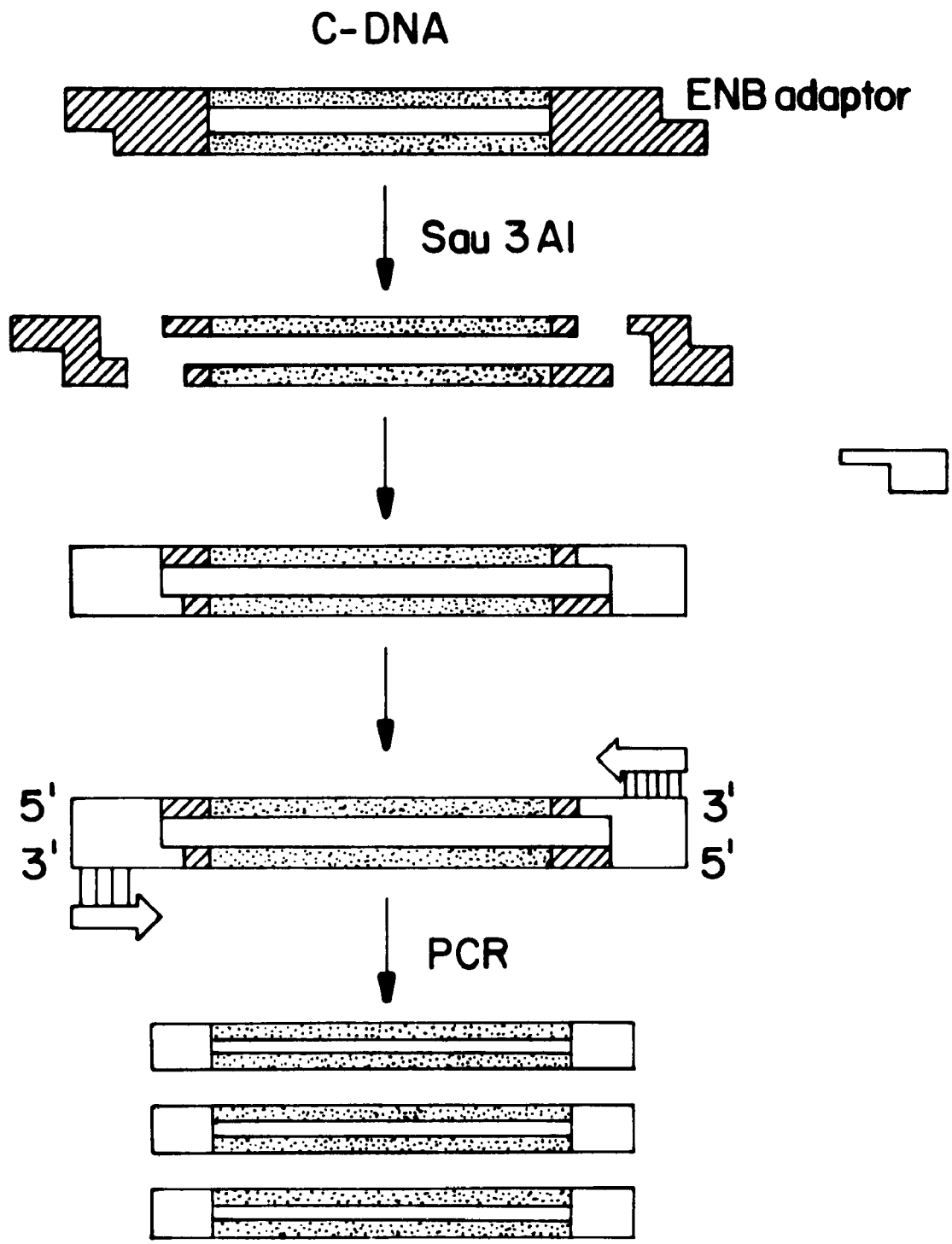
FIG. 2 is a schematic diagram of the "shot-gun" PCR method used to prepare cDNA probes for library screening.

Total RNAs from HAC2/P and HAC2/0.4 ($5 \times 10^7$ cells each) were prepared using a commercially available RNA isolation kit (from Stratagene). Poly(A)+RNAs were obtained by ologo(dt)-cellulose chromatography using standard methods. Oligo(dt)-primed cDNAs were prepared from isolated poly(A)+RNA using a commercially available cDNA synthesis kit (CDNA Synthesis System Plus from Amersham). The cDNAs were ligated to 20 pmol of ENB adaptor (commercially obtained from Takara) in a 10 μl of reaction volume including 4 μl of ligation stock buffer [66 mM Tris-HCl(pH 7.6), 6.6 mM $MgCl_2$, 10 mM dithiothreitol], 2 μl of 10 mM ATP and 1 μl of T4 DNA Ligase (commercially obtained from Takara). After ligation, the cDNAs were precipitated with NH4OAc/isopropyl alcohol, washed with 70% ethanol and dissolved in $H_2O$. The cDNAs, with ENB adaptor, were added to a 16 μl reaction volume including 10 μl of phosphorylation stock buffer [100 mM Tris-HCl (pH 7.6), 20 mM $MgCl_2$, 20 mM 2-mercaptoethanol], 1 μl of 10 mM ATP and 50 units of Kinase (commercially obtained from Takara) and incubated for 50 min at 37° C. for phosphorylation. After phosphorylation, the samples were extracted with phenol/chloroform, precipitated with $NH_4OAc$/isopropyl alcohol, washed with 70% ethanol and dissolved in TE buffer. Half of the total cDNA from each cell line was gel purified using glass beads (Gene Clean Kit; Bio 101). One-fifth volume of cDNA with ENB adaptor from HAC2/0.4 was ligated to λZAPII using a λZAPII cloning kit (commercially obtained from Stratagene) and packaged using Gigapack Gold (commercially obtained from Stratagene). The titer of cDNA from HAC2/0.4 was approximately $10^6$ recombinants. Another ⅕ volume of cDNAs with ENB adaptor from HAC2/P and HAC2/0.4 was digested by SauIII-A1 (commercially obtained from Takara) for further probe preparation (see below).

cDNA Probe Preparation cDNA probes for library screening were prepared by a "shot-gun" PCR method summarized schematically in FIG. 2 and described as follows: A synthetic adaptor was constructed by annealing an oligonucleotide of the sequence 5'-GATCTCGTTCGCTTC GTCTGTCT-3' (referred to as GATC (-); SEQ ID NO: 3) with a complimentary oligonucleotide of the sequence 5'-AGACAGACGAAAGCGAACGA-3' (SEQ ID NO: 4) at a concentration of 570 pmol for each chain. The adaptor was kinased at the 5' ends in a 100 μl reaction volume including 10 μl of T4 polynucleotide kinase (commercially obtained from Takara), 20 μl of PNK stock buffer [250 mM Tris-HCl (pH 7.6), 50 mM $MgCl_2$, 50 mM 2-mercaptoethanol], 2 μl of 100 mM ATP. The oligonucleotides were synthesized on an ABI DNA synthesizer. The cDNAs, with ENB adaptor, from HAC2/P and HAC2/0.4, digested with SauIII-A1 (prepared as described above), were ligated to this synthetic adaptor containing a SauIII-A1 site in a 20 μl total reaction volume including 4 μl of ligation stock buffer [330 mM Tris-HCl (pH 7.6), 33 mM $MgCl_2$, 50 mM dithiothreitol], 2 μl of 10 mM ATP and 1 μl of T4 DNA ligase (commercially obtained from Takara).

Amplification of the cDNAs (ligated to the adaptor) by PCR was carried out by 30 consecutive cycles of 94° C. for 30 seconds, primer annealing at 55° C. for 30 seconds, and polymerization at 72° C. for 3 min. in a DNA thermal cycler (Perkin-Elmer Cetus). The GATC (-) oligonucleotide was used as primer (previously prepared in adaptor construction, described above) in a 100 μl reaction volume including 10 μl of PCR stock buffer [100 mM Tris (pH 9), 500 mM KCl, 1% TritonX-100, 15 mM $MgCl_2$], 2 μl of 10 mM dNTPs, 150 pmol of GATC (-) primer and 1 μl of Amplitaq (Promega). After amplification, the PCR products were analyzed by agarose gel electrophoresis and routinely gave a smear pattern. PCR products were purified using glass beads (Gene Clean Kit; Bio 101) to be used as probes in plaque hybridization, described below.

Differential Library Screening

After packaging of the cDNA library from HAC2/0.4 ($10^6$ recombinants) (prepared as described above), phage solution was diluted in SM buffer and plated on E. coli pBluescript competent cells (commercially obtained from Stratagene) at a density of $10^3$ plaques per 15 cm dish. Lifts were taken in quadruplicate onto nylon filters (Hybond+, commercially obtained from Amersham). Filters were washed extensively with 0.5 M NaCl, 0.5 M NaOH for 5 minutes and with 1.5 M NaCl, 0.5 M Tris-HCl for 20 minutes. Filters were crosslinked by UV fixation, and prehybridized with a blocking solution (ECL: Direct Nucleotide Labeling & Detection System, Amersham). For differential cloning, duplicate filters were hybridized with the same solution containing 10 ng/ml labeled probe from HAC2/P and HAC2/0.4 respectively (previously prepared by PCR as described above) for 4 hrs at 42° C. (ECL: Direct Nucleotide Labeling & Detection System, Amersham). Probes were labeled according to the manufacturer's instructions. $10^5$ recombinant phages were plated and screened. After hybridization, the filters were subjected to autoradiography using Kodak XAR film. The positive plaques, which were overexpressed in HAC2/0.4 cDNA but not in HAC2/P cDNA, were picked and purified through two additional rounds of screening. Positive clones were rescued as pBluescript plasmids according to the manufacture's instruction (Stratagene).

EXAMPLE 2

Expression of cDNA62 Isolated by Differential Screening of a HAC2/0.4 cDNA Library Differential screening of the HAC2/0.4 cDNA library with cDNA probes from HAC2/P and HAC2/0.4, as described in Example 1, led to the isolation of a cDNA clone termed cDNA62. The full-length cDNA62 (cDNA62F) in pBluescript SK⁻ plasmid has been deposited at the National Institute of Bioscience and Human Technology in Tsukubashi, Ibaraki-ken 305, Japan, in compliance with the provisions of the Budapest Treaty, and has been assigned Deposit No. FERM BP-4629.

cDNA62 was used as a probe in Northern blot experiments to determine the expression of cDNA62 in cisplatin sensitive and resistant cancer cell lines and in human tissues. For Northern analysis, 4 µg of poly(A)+RNA were separated by electrophoresis on a 1% agarose, 2.2 M formaldehyde gel and blotted onto a nylon filter (Hybond+; commercially obtained from Amersham). The filters were prehybridized in blocking solution (described above for plaque filter hybridization) for 12 hrs at 42° C.; hybridized in the same solution with labeled full length cDNA insert; washed twice in washing solution for 10 min at room temperature, in 20×SSC for 10 min. at room temperature; and submitted to autoradiography using Kodak XAR film.

Figure 3:
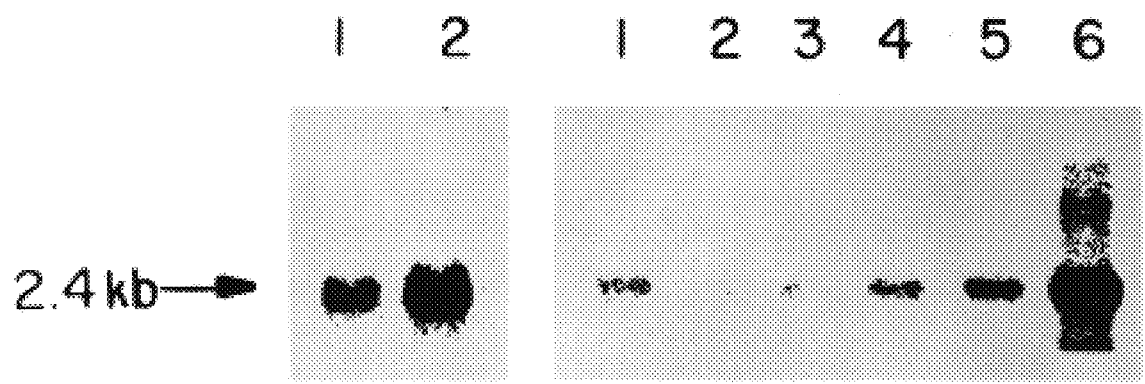
FIG. 3A is a photograph of a Northern blot depicting the expression of cDNA62 in the HAC2/P cell line (lane 1) and the HAC2/0.4 cell line (lane 2).
FIG. 3B is a photograph of a Northern blot depicting the expression of cDNA62 in the following cells: untransfected NIH3T3 cells in the absence of dexamethasone (lane 1); untransfected NIH3T3 cells in the presence of dexamethasone (lane 2); NIH3T3 cells transfected with pMAMneo in the absence of dexamethasone (lane 3); NIH3T3 cells transfected with pMAMneo in the presence of dexamethasone (lane 4); NIH3T3 cells transfected with pMAMneo62F-1-3 in the absence of dexamethasone (lane 5); NIH3T3 cells transfected with pMAMneo62F-1-3 in the presence of dexamethasone (lane 6).
Figure 4:
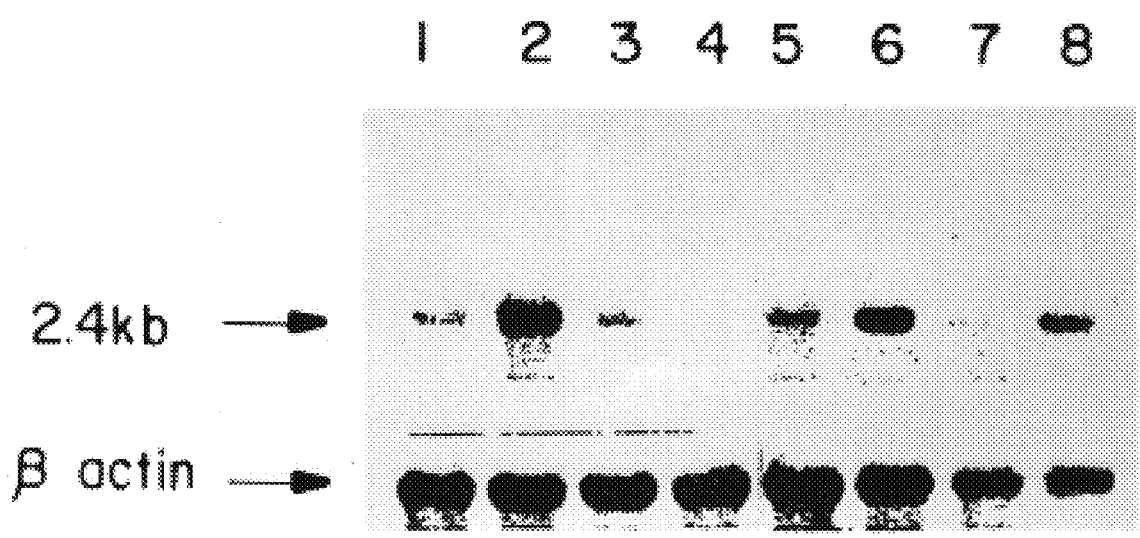
FIG. 4 is a photograph of a Northern blot depicting the expression of cDNA62 in the following lung cancer cell lines: L231 (lane 1); L231/CDDP resistant (lane 2); PC7 (lane 3); PC7/CDDP resistant (lane 4); PC9 (lane 5); PC9/CDDP resistant (lane 6); PC14 (lane 7). PC14/CDDP resistant (lane 8).

The expression of cDNA62 was examined in ovarian and lung cancer cell lines. FIG. 3A depicts the expression of cDNA62 in the ovarian cancer cell line HAC2/P (lane 1) versus HAC2/0.4 (lane 2), its cisplatin resistant derivative from which cDNA62 was cloned. The results demonstrate the increased expression of cDNA62 in the cisplatin resistant HAC2/0.4 cell line. FIG. 4 depicts the expression of cDNA62 in four cisplatin resistant derivative cell lines: L231/R (lane 2), PC7/R (lane 4), PC9/R (lane 6) and PC14/R (lane 8) and their respective parental cell lines (lanes 1, 3, 5 and 7, respectively). The results demonstrate that cDNA62 expression is elevated in 3 of the 4 cisplatin resistant cell lines (L231/R, PC9/R and PC14/R) relative to their parental lines. Thus, 4 out of 5 cisplatin resistant cancer cell lines examined exhibited increased expression of cDNA62 relative to their parental cell lines.

Figure 5A:
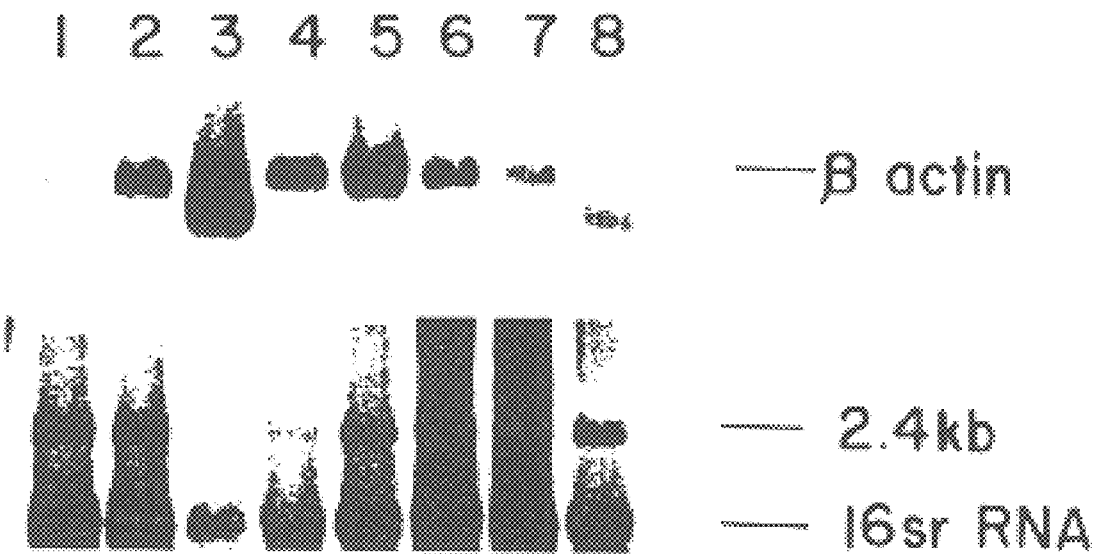
FIG. 5 is a photograph of Northern blots depicting the expression of cDNA62 in the following human tissues: heart (lane 1); brain (lane 2); placenta (lane 3); lung (lane 4); liver (lane 5); skeletal muscle (lane 6); kidney (lane 7); pancreas (lane 8); spleen (lane 9); thymus (lane 10); prostate (lane 11); testis (lane 12); ovary (lane 13); small intestine (lane 14); colon (lane 15); peripheral blood leukocytes (lane 16).
Figure 5B:
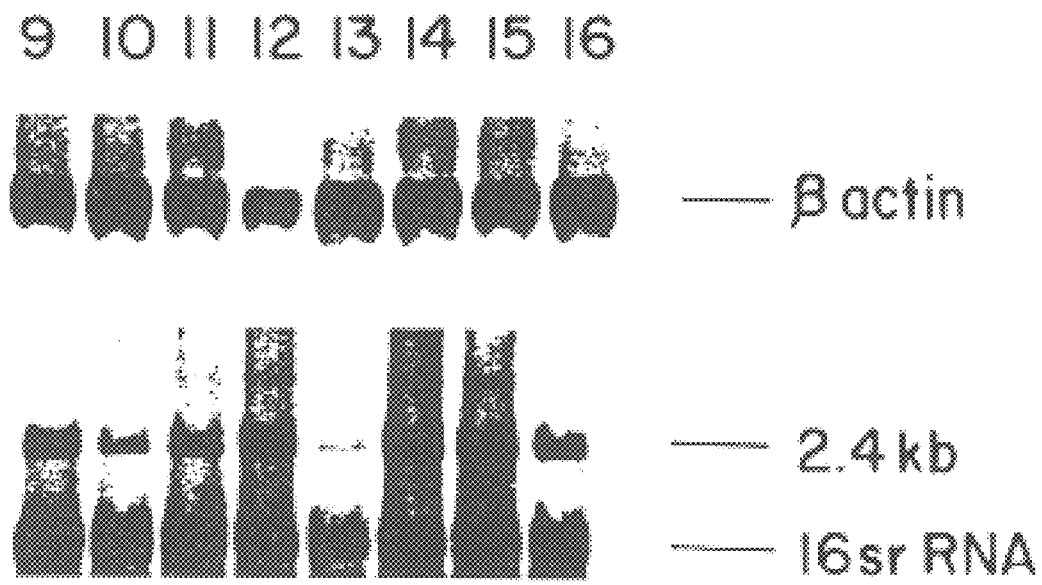

The expression of cDNA62 was also examined in normal human tissue by Northern analysis using Human Multiple Tissue Northern Blot I and II (commercially obtained from Clontech) and labeled cDNA62 as the probe. The results are shown in FIG. 5, wherein the 2.4 kb band corresponds to cDNA62. Relatively higher levels of cDNA62 expression were seen in brain (lane 2), kidney (lane 7), colon (lane 15), pancreas (lane 8), and liver (lane 5). Malignant tumors of these tissues are known to have low sensitivity to cisplatin. In comparison, relatively lower levels of cDNA62 were seen in placenta (lane 3), ovary (lane 13) and lung tissue (lane 4), which correlates with the relatively greater sensitivity of placental choriocarcinoma, ovarian carcinoma and lung cancer to cisplatin.

Thus, the results of these studies examining the expression pattern of cDNA62 in cell lines and tissues indicate that the expression of cDNA62 is associated with cisplatin resistance.

EXAMPLE 3

Sequence Analysis of cDNA62 cDNA62 was excised from phage directly as pBluescript plasmid. The cDNA insert was approximately 2.6 kb in length. The nucleotide sequence of the entire cDNA insert was determined by the standard dye termination method using an autosequencer (ABI Model 373A). Additional sequence information for both strands was obtained by the standard dideoxy chain-termination method. The nucleotide sequence of cDNA62 is shown in FIG. 6 and SEQ ID NO: 1. The cDNA62 sequence was compared for homology with sequences of the Swiss data library. This analysis demonstrated that cDNA62 is 99.6% homologous to the human mitochondrial DNA fragment extending from the 16S rRNA gene through the tRNA$^{Leu}$ gene and the ND1 gene up to the tRNA$^{Ile}$ gene (except that cDNA62 lacks the first 34 base pairs of the 16S rRNA gene). The nucleotide sequence of cDNA62 is compared to that of mitochondrial DNA in FIG. 6.

cDNA62 has a 5' untranslated region of 1598 base pairs, followed by an open reading frame encoding 83 amino acids (extending from nucleotides 1599 to 1847) and a stop codon. In contrast, the position corresponding to the stop codon in cDNA62 codes for a tryptophan residue in the mitochondrial ND1 gene (i.e., UGA in nuclear mRNA is translated as a stop codon but is translated as Trp in mitochondrial mRNA). Thus, translation of the mitochondrial ND1 transcript extends beyond amino acid 83 and the protein encoded by cDNA62 corresponds to the first (N-terminal) 83 amino acid of the ND1 protein. In cDNA62, nucleotide sequences following the stop codon at amino acid position 84 (i.e., nucleotides 1848 to 2564) are 3' untranslated sequences.

Figure 7A:
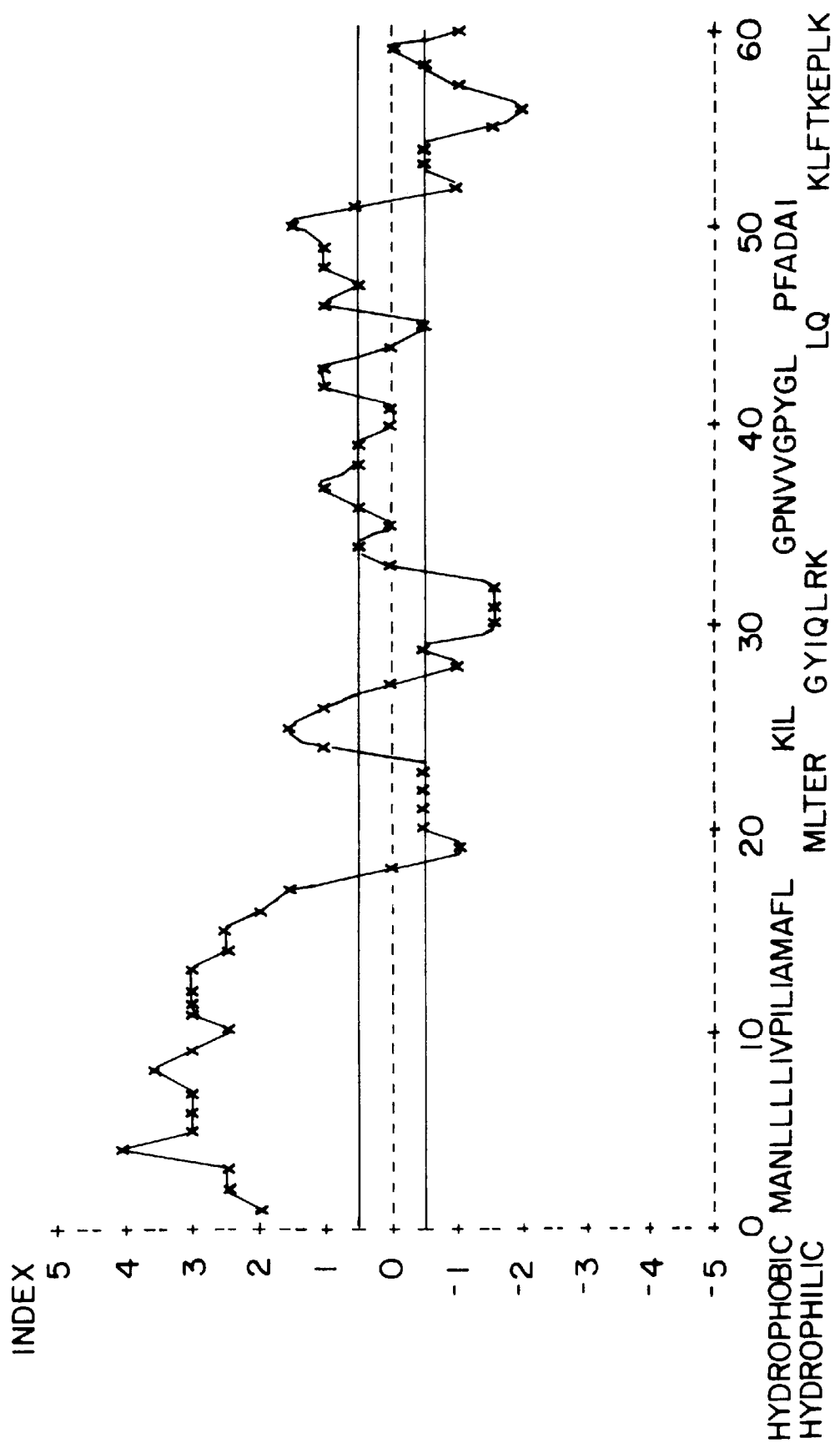
FIG. 7 is a graph depicting the hydrophobicity of the protein encoded by cDNA62. A positive index indicates hydrophobicity whereas a negative index indicates hydrophilicity.

The hydrophobicity of the protein encoded by cDNA62 is plotted graphically in FIG. 7. The hydrophobicity analysis revealed several hydrophobic stretches, consistent with the protein being localized to a cell membrane.

EXAMPLE 4 cDNA62 Confers Resistance to Cisplatin on a Host Cell

Construction of Recombinant Expression Vectors

Figure 8:
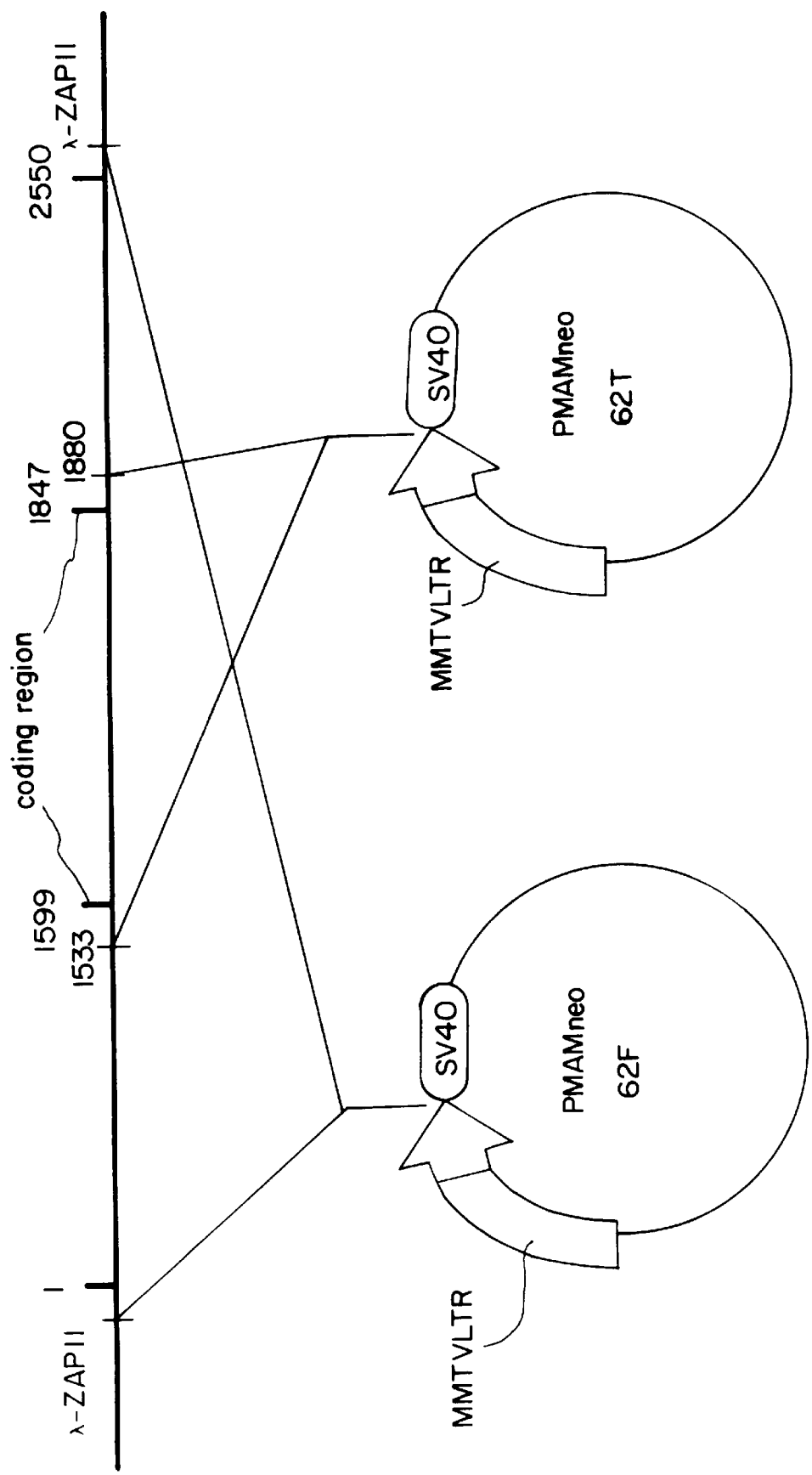
FIG. 8 is a schematic diagram depicting the construction of the recombinant expression vectors pMAMneo62F and PMAMneo62T.

To express cDNA62 in a host cell, the full-length cDNA and the coding region of the cDNA were each subcloned into the expression vector PMAMneo (commercially obtained from Clontech). In PMAMneo, the inserted cDNA sequences are linked at the 5' end to a dexamethasone inducible MMTV-LTR and at the 3' end to SV40 polyadenylation sequences. The vector also contains sequences encoding neomycin resistance, allowing for selection of cells transfected with the plasmid with G418. For the full-length construct, a 2.6 kb SmaI-XhoI fragment of cDNA62 in pBluescript was gel purified and ligated into PMAMneo cut with XhoI and NheI, the NheI overhang of PMAMneo being filled in with T4 DNA polymerase (obtained from Takara). This gave construct PMAMneo62F. For the expression of the coding region of cDNA62, cDNA62 in pBluescript was cut by HincII and the resulting fragment was gel purified. This HincII fragment was then cut with HapII and blunted. This fragment corresponds to approximately nucleotides 1533 to 1880 and encompasses the coding region of cDNA62 (nucleotides 1599 to 1847). This fragment was cloned to PMAMneo which had been cut with NheI and blunted. This gave construct PMAMneo62T. The two expression vectors, PMAMneo62F and PMAMneo62T, are diagrammed schematically in FIG. 8.

Transfections

NIH3T3 cells (5×10)⁵, in 10 cm dishes, were transfected for 18 hrs by the standard calcium phosphate method. Transfections included 5 µg of full length cDNA62 plasmid (PMAMneo62F), truncated cDNA62 plasmid (PMAMneo62F) or vector control (PMAMneo). At the end of transfection, the cells were washed once with PBS, fed with growth medium of DMEM/10% calf serum and incubated for 24 hrs before trypsinization and splitting. G418 (commercially obtained from Sigma) was added at 0.4 mg/ml 24 hrs after splitting. Selection was continued for 10–14 days, at which time several colonies were evident. These colonies were isolated and expanded in growth medium containing G-418 and used for analysis of cisplatin sensitivity using an MTT assay. The expression of cDNA62 in transfected and untransfected cells was examined by Northern analysis. The results are shown in FIG. 3B.

Untransfected NIH3T3 cells in the absence (lane 1) or presence (lane 2) of dexamethasone, NIH3T3 cells transfected with the parental pMAMneo plasmid in the absence (lane 3) or presence (lane 4) of dexamethasone, and NIH3T3 cells transfected with pMAMneo62F in the absence of dexamethasone (lane 5) all display low or undetectable levels of expression of cDNA62. In contrast, NIH3T3 cells transfected with pMAMneo62F in the presence of dexamethasone (lane 6) shows a much greater level of expression of cDNA62. Similar results were seen in NIH3T3 cells transfected with pMAMneo62T upon induction with dexamethasone.

MTT assay

The sensitivity to cisplatin of NIH3T3 cells transfected with a cDNA62 expression vector or with the pMAMneo parental vector were tested using an MTT assay. The cell lines were pretreated without or with dexamethasone at a concentration of 2.0 μM for induction of insert cDNA 48 hrs before plating. The cells, at a density of $1 \times 10^3$ cells per well, were plated in 180 μl of medium in 96-well plates in the presence of various concentrations of cisplatin. After 4 days of incubation at 37° C., the medium was aspirated from the wells as completely as possible. 200 μl of dimethyl sulfoxide was added to each well. The plates were then agitated on a plate shaker for 5 min. and the optical density was read using a Titertek Multiscan MCC plate reader. The sensitivity to cisplatin of the control and transfected cell lines in the absence (−) or presence of dexamethasone is expressed as the $IC_{50}$ (the concentration of drug which reduces the cell growth to 50% of control). The results are shown in Table 1.

TABLE 1

Sensitivity of Transfectants and Controls to CDDP Expressed as the $IC_{50}$(μg/ml)

| | |
|---|---|
| NIH3T3 (−) | 0.21 ± 0.09 |
| NIH3T3 (+) | 0.22 ± 0.08 |
| pMAMneo (−) | 0.25 ± 0.05 |
| pMAMneo (+) | 0.28 ± 0.09 |
| pMAMneo62F-1-3 (−) | 0.29 ± 0.18 |
| pMAMneo62F-1-3 (+) | 3.8 ± 0.15* |
| pMAMneo62T-3-1 (−) | 0.27 ± 0.08 |
| pMAMneo62T-3-1 (+) | 2.2 ± 0.15* |

*:P < 0.01

Cells transfected with the pMAMneo62F plasmid and induced with dexamethasone exhibited approximately 18-fold greater resistance to cisplatin as compared with that of untransfected NIH3T3 cells in the absence of dexamethasone. Similarly, cells transfected with the pMAMneo62T plasmid and induced with dexamethasone exhibited approximately 10-fold greater resistance to cisplatin as compared with that of untransfected NIH3T3 cells in the absence of dexamethasone. Thus, both the full-length cDNA62 and the coding region of cDNA62 are capable of conferring high level (i.e., greater than a 5-fold increase in) cisplatin resistance when expressed in a host cell.

EXAMPLE 5 cDNA62 Confers Resistance to Cadmium and Copper on a Host Cell

To test the sensitivity of cells transfected with cDNA62 to heavy metals, the NIH3T3 cell transfectants, as described in Example 4, were cultured with various concentrations of cadmium or copper, in the presence or absence of dexamethasone. Cell cytotoxicity was measured by the MTT assay described in Example 4 and the results are shown in Table 2 expressed as $IC_{50}$ values.

TABLE 2

Sensitivity of Transfectants and Controls to Cadmium (Cd) and Copper (Cu) Expressed as the $IC_{50}$(μg/ml)

| | Cd | Cu |
|---|---|---|
| NIH3T3 (−) | 0.15 ± 0.09 | 1.9 ± 0.05 |
| NIH3T3 (+) | 0.18 ± 0.09 | 2.2 ± 0.09 |
| pMAMneo (−) | 0.21 ± 0.15 | 2.4 ± 0.15 |
| pMAMneo (+) | 0.27 ± 0.12 | 2.5 ± 0.14 |
| pMAMneo62F-1-3 (−) | 0.31 ± 0.12 | 2.6 ± 0.21 |
| pMAMneo62F-1-3 (+) | 2.1 ± 0.11* | 8.1 ± 0.05* |

*:P < 0.05

Cells transfected with the pMAMneo62F plasmid and induced with dexamethasone exhibited approximately 15-fold greater resistance to cadmium and 4-fold greater resistance to copper as compared with that of untransfected NIH3T3 cells in the absence of dexamethasone. Thus, in addition to conferring resistance to cisplatin, cDNA62 can confer high level resistance to other heavy metals, such as copper and cadmium, on a host cell.

EXAMPLE 6

Specificity of cDNA62-Mediated Resistance to Anti-Cancer Agents

To test the sensitivity of cells transfected with cDNA62 to other anti-cancer agents, the NIH3T3 cell transfectants, as described in Example 4, were cultured with various concentrations of CBDCA, adriamycin, melphalan or CPT-11, in the presence or absence of dexamethasone. Cell cytotoxicity was measured by the MTT assay described in Example 4 and the results are shown in Table 3 expressed as $IC_{50}$ values.

TABLE 3

Sensitivity of Transfectants and Controls to Anti-Cancer Agents Expressed as the $IC_{50}$(μg/ml)

| | CDBCA | Adriamycin | Melphalan | CPT-11 |
|---|---|---|---|---|
| NIH3T3 (−) | 5.5 ± 0.09 | 0.19 ± 0.05 | 1.21 ± 0.15 | 10.5 ± 0.19 |
| pMAMneo62F-1-3 (+) | 15 ± 0.25 | 0.18 ± 0.10 | 9.8 ± 0.25* | 15.0 ± 0.27 |

*:P < 0.05

Cells transfected with the pMAMneo62F plasmid and induced with dexamethasone exhibited a statistically significant increase in resistance to melphalan (approximately 8-fold greater resistance than untransfected NIH3T3 cells in the absence of dexamethasone) but did not exhibit an increase in resistance to CDBCA, adriamycin or CPT-11. These results indicate that there is specificity in the resistance conferred by cDNA62 on a host cell.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. An isolated human protein which confers on a cell in which the protein is expressed at least a 5-fold increase in cisplatin resistance relative to a cisplatin sensitive cell, wherein the protein is encoded by a nucleotide sequence which is translated in the cytoplasm, the protein being an amino-terminal portion of an ND-1 subunit of NADH-ubiquinone oxidoreductase.

2. The protein of claim 1 which confers at least a 10-fold increase in cisplatin resistance relative to a cisplatin sensitive cell.

3. The protein of claim 1 which confers at least a 15-fold increase in cisplatin resistance relative to a cisplatin sensitive cell.

4. The protein of claim 1 which further confers cadmium resistance on a cell in which the protein is expressed relative to a cadmium sensitive cell.

5. The protein claim 1 which further confers copper resistance on a cell in which the protein is expressed relative to a copper sensitive cell.

6. The protein of claim 1 which comprises a sequence encoded by a nucleic acid which hybridizes to SEQ ID NO:1 in 0.2×SSC between 50° and 65° C.

7. An isolated protein which confers cisplatin resistance on a cell in which the protein is expressed comprising an amino acid sequence shown in SEQ ID NO: 2.

8. The protein of claim 7, or portion thereof, which is immunogenic.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 2564 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 1599..1847

(xi) SEQUENCE DESCRIPTION: SEQ ID NO:1:

```
CTTAGCCAAA CCATTTACCC AAATAAAGTA TAGGCGATAG AAATTGAAAC CTGGCGCAAT       60

AGATATAGTA CCGCAAGGGA AAGATGAAAA ATTATAACCA AGCATAATAT AGCAAGGACT      120

AACCCCTATA CCTTCTGCAT AATGAATTAA CTAGAAAATA CTTTGCAAGG AGAGCCAAAG      180

CTAAGACCCC CGAAACCAGA CGAGATACCT AAGAACAGCT AAAAGAGCAC ACCCGTATAT      240

GTACCAAAAT AGTGGGAAGA TTTATAGGTA GAGGCGACAA ACCTACCGAG CCTGGTGATA      300

GCTGGTTGTC CAAGATAGAA TCTTAGTTCA ACTTTAAATT TGCCCACAGA ACCCTCTAAA      360

TCCCCTTGTA AATTTAACTG TTAGTCCAAA GAGGAACAGC TCTTTGGACA CTAGGAAAAA      420

ACCTTGTAGA GAGAGTAAAA AATTTAACAC CCATAGTAGG CCTAAAAGCA GCCACCAATT      480

AAGAAAGCGT TCAAGCTCAA CACCCACTAC CTAAAAAATC CAAACATAT AACTGAACTC       540

CTCACACCCA ATTGGACCAA TCTATCACCC TATGAAGAA CTAATGTTAG TATAAGTAAC       600

ATGAAAACAT TCTCCTCCGC ATAAGCCTGC GTCAGATTAA ACACTGAAC TGACAATTAA       660

CAGCCCAATA TCTACAATCA ACCAACAAGT CATTATTACC CTCACTGTCA ACCCAACACA      720

GGCATGCTCA TAAGGAAAGG TTAAAAAAAG TAAAAGGAAC TCGGCAAATC TTACCCCGCC      780

TGTTTACCAA AAACATCACC TCTAGCATCA CCAGTATTAG AGGCACCGCC TGCCCAGTGA      840

CACATGTTTA ACGGCCGCGG TACCCTAACC GTGCAAAGGT AGCATAATCA CTTGTTCCTT      900

AAATAGGGAC CTGTATGAAT GGCTCCACGA GGTTCAGCTG TCTCTTACTT TTAACCAGTG      960

AAATTGACCT GCCCGTGAAG AGGCGGGCAT GACACAGCAA GACGAGAAGA CCCTATGGAG     1020

CTTTAATTTA TTAATGCAAA CAGTACCTAA CAAACCCACA GGTCCTAAAC TACCAAACCT     1080

GCATTAAAAA TTTCGGTTGG GGCGACCTCG GAGCAGAACC CAACCTCCGA GCAGTACATG     1140

CTAAGACTTC ACCAGTCAAA GCGAACTACT ATACTCAATT GATCCAATAA CTTGACCAAC     1200

GGAACAAGTT ACCCTAGGGA TAACAGCGCA ATCCTATTCT AGAGTCCATA TCAACCAATA     1260

GGGTTTACGA CCTCGATGTT GGATCCAGGA CATCCCGATG GTGCAGCCGC TATTAAAGGT     1320

TCGTTTGTTC AGCGATTAAA GTCCTACGTG ATCTGAGTTC AGACCGGAGT AATCCAGGTC     1380

GGTTTCTATC TACTTCAAAT TCCTCCCTGT ACGAAAGGAC AAGAGAAATA AGGCCTACTT     1440

CACAAAGCGC CTTCCCCCGT AAATGATATC ATCTCAACTT AGTATTATAC CCACACCCAC     1500

CCAAGAACAG GGTTTGTTAA GATGGCAGAG CCCGGTAATC GCATAAAACT TAAAACTTTA     1560

CAGTCAGAGG TTCAATTCCT CTTCTTAACA ACATACCC ATG GCC AAC CTC CTA         1613
                                            Met Ala Asn Leu Leu
                                            1               5
```

```
CTC CTC ATT GTA CCC ATT CTA ATC GCA ATG GCA TTC CTA ATG CTT ACC      1661
Leu Leu Ile Val Pro Ile Leu Ile Ala Met Ala Phe Leu Met Leu Thr
 10              15                  20

GAA CGA AAA ATT CTA GGC TAT ATA CAA CTA CGC AAA GGC CCC AAC GTT      1709
Glu Arg Lys Ile Leu Gly Tyr Ile Gln Leu Arg Lys Gly Pro Asn Val
         25                  30                  35

GTA GGC CCC TAC GGG CTA CTA CAA CCC TTC GCT GAC GCC ATA AAA CTC      1757
Val Gly Pro Tyr Gly Leu Leu Gln Pro Phe Ala Asp Ala Ile Lys Leu
 40                  45                  50

TTC ACC AAA GAG CCC CTA AAA CCC GCC ACA TCT ACC ATC ACC CTC TAC      1805
Phe Thr Lys Glu Pro Leu Lys Pro Ala Thr Ser Thr Ile Thr Leu Tyr
         55                  60                  65

ATC ACC GCC CCG ACC TTA GCT CTC ACC ATC GCT CTT CTA CTA TGAACCCCCC   1857
Ile Thr Ala Pro Thr Leu Ala Leu Thr Ile Ala Leu Leu Leu
 70                  75                  80

CTCCCCATAC CCAATCCCCT GGTCAACCTC AACCTAGGCC TCCTATTTAT TCTAGCCACC    1917

TCTAGCCTAG CCGTTTACTC AATCCTCTGA TCAGGGTGAG CATCAAACTC AAACTACGCC    1977

CTGATCGGCG CACTGCGAGC AGTAGCCCAA ACAATCTCAT ATGAAGTCAC CCTAGCCATC    2037

ATTCTACTAT CAACATTACT AATAAGTGGC TCCTTTAACC TCTCCACCCT TATCACAACA    2097

CAAGAACACC TCTGATTACT CCTGCCATCA TGACCCTTGG CCATAATATG ATTTATCTCC    2157

ACACTAGCAG AGACCAACCG AACCCCCTTC GACCTTGCCG AAGGGGAGTC CGAACTAGTC    2217

TCAGGCTTCA ACATCGAATA CGCCGCAGGC CCCTTCGCCT TATTCTTCAT AGCCGAATAC    2277

ACAAACATTA TTATAATAAA CACCCTCACC ACTACAATCT TCCTAGGAAC AACATAAGAC    2337

GCACTCTCCC CTGAACTCTA CACAACATAT TTTGTTACCA AGACCCTACT TCTAACCTCC    2397

CTGTTCTTAT GAATTCGAAC AGCATACCCC CGATTCCGCT ACGACCAACT CATACACCTC    2457

CTATGAAAAA ACTTCCTACC ACTCACCCTA GCATTACTTA TATGATATGT CTCCATACCC    2517

ATTACAATCT CCAGCATTCC CCCTCAAACC TAAAAAAAAA AAAAAA                   2564

(2) INFORMATION FOR SEQ ID NO:2:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Asn Leu Leu Leu Ile Val Pro Ile Leu Ile Ala Met Ala
 1               5                  10                  15

Phe Leu Met Leu Thr Glu Arg Lys Ile Leu Gly Tyr Ile Gln Leu Arg
         20                  25                  30

Lys Gly Pro Asn Val Val Gly Pro Tyr Gly Leu Leu Gln Pro Phe Ala
 35                  40                  45

Asp Ala Ile Lys Leu Phe Thr Lys Glu Pro Leu Lys Pro Ala Thr Ser
         50                  55                  60

Thr Ile Thr Leu Tyr Ile Thr Ala Pro Thr Leu Ala Leu Thr Ile Ala
 65                  70                  75                  80

Leu Leu Leu (2) INFORMATION FOR SEQ ID NO:3:

(i) SEQUENCE CHARACTERISTICS:
        (A) LENGTH: 23 base pairs
```

```
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:3:

GATCTCGTTC GCTTCGTCTG TCT                                              23

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:4:

AGACAGACGA AAGCGAACGA                                                  20
```